(12) United States Patent
Kim et al.

(10) Patent No.: US 11,872,263 B2
(45) Date of Patent: *Jan. 16, 2024

(54) AIMP1 PROTEIN FRAGMENT AND HAIR GROWTH-PROMOTING COMPOSITION CONTAINING SAME AS ACTIVE INGREDIENT

(71) Applicant: CUREBIO THERAPEUTICS, Gyeonggi-Do (KR)

(72) Inventors: Sunghoon Kim, Seoul (KR); Min Chul Park, Gyeonggi-do (KR); Younha Kim, Gyeonggi-do (KR)

(73) Assignee: CUREBIO THERAPEUTICS, Gyeonggi-Do (KR)

( * ) Notice: Subject to any disclaimer, the term of this patent is extended or adjusted under 35 U.S.C. 154(b) by 40 days.

This patent is subject to a terminal disclaimer.

(21) Appl. No.: 17/213,472

(22) Filed: Mar. 26, 2021

(65) Prior Publication Data
US 2021/0244793 A1   Aug. 12, 2021

Related U.S. Application Data

(63) Continuation of application No. 16/320,404, filed as application No. PCT/KR2017/008078 on Jul. 27, 2017, now Pat. No. 11,311,601.

(30) Foreign Application Priority Data

Jul. 28, 2016  (KR) .................. 10-2016-0096256

(51) Int. Cl.
| | | |
|---|---|---|
| *A61K 38/10* | (2006.01) | |
| *A61K 38/17* | (2006.01) | |
| *A23L 33/18* | (2016.01) | |
| *A61P 1/14* | (2006.01) | |
| *A61K 8/64* | (2006.01) | |
| *A61Q 7/00* | (2006.01) | |

(52) U.S. Cl.
CPC .............. *A61K 38/17* (2013.01); *A23L 33/18* (2016.08); *A61K 8/64* (2013.01); *A61P 1/14* (2018.01); *A61Q 7/00* (2013.01)

(58) Field of Classification Search
None
See application file for complete search history.

(56) References Cited

U.S. PATENT DOCUMENTS

| | | | | |
|---|---|---|---|---|
| 7,763,587 | B2 * | 7/2010 | Michelet ................ | A61Q 5/006 514/25 |
| 11,311,601 | B2 * | 4/2022 | Kim ........................ | A23L 33/18 |
| 2009/0305973 | A1 | 12/2009 | Kim et al. | |
| 2010/0167997 | A1 | 7/2010 | Kim | |

FOREIGN PATENT DOCUMENTS

| | | |
|---|---|---|
| CN | 101370821 A | 2/2009 |
| JP | 2008528577 A | 7/2008 |
| JP | 2009-523844 A | 6/2009 |
| JP | 2019-527105 | 9/2019 |
| KR | 10-1993-0701176 A | 6/1993 |
| KR | 10-1020658 B1 | 3/2011 |
| WO | WO 90/06117 | 6/1990 |
| WO | WO 2007/083853 | 7/2007 |
| WO | WO 2007/083853 A1 | 7/2007 |

OTHER PUBLICATIONS

Wei-hong Lin, et al., "Fibroblast Growth Factors Stimulate Hair Growth through β-Catenin and Shh Expression in C57BL/6 Mice," BioMed Research International, vol. 2015, 9 pages.
Age, seasonal hair loss . . . It's a big deal if you're young! Article Entry, Oct. 20, 2009, 10:53:43.
International Search Report in corresponding PCT Application No. PCT/KR2017/008078, dated Nov. 8, 2017.
Park, DuWoN, "Hair Loss Irrelevant to Age and Season . . . Pay Attention to it even Young," MK News, Oct. 27, 2009, p. 1, Internet; <URL:http://news.mk.co.kr/newsReadPrint_2013.php?year=2009&no=543269>.
Park. Sang Gyu et al., "Aminoacyl-tRNA Synthetase-interacting Multifunctional Proteins (AlMPs): A Triad for Cellular Homeostasis," IUBMB Life, Apr. 2010, vol. 62, No. 4, pp. 296-302.
Kim, Seo Yoon et al., "ARS-interacting Multi-functional Protein 1 Induces Proliferation of Human Bone Marrow-derived Mesenchymal Stem Cells by Accumulation of B-catenin via Fibroblast Growth Factor Receptor 2-mediated Activation of Akt" Stem Cells and DevelOpment, May 14, 2013 (online), vol. 22, No. 19, pp. 2630-2640.
Peason W ("An introduction to sequence similarity ("Homology") searching" Curr Protoc Bioinformatics Jun. 2013 printed as pp. 1-9) (Year: 2013).
Piyush et al. ("A review of benzopyran derivatives in pharmacotherapy of breast cancer" Asian Journal of Pharmaceutical and Clinical Research v11 (7) 2018 pp. 43-46) (Year: 2018).
CureBio website entry retrieved from http://www.cure-bio.com/en/neopep_a1h/ on Nov. 19, 2020, 1 page (Year: 2020).

(Continued)

*Primary Examiner* — Ronald T Niebauer
(74) *Attorney, Agent, or Firm* — LEASON ELLIS LLP

(57) ABSTRACT

The present invention relates to novel fragments of AIMP1 protein and a composition for improving alopecia and promoting hair growth comprising the same, more specifically it relates to a polypeptide consisting of 4 to 21 consecutive amino acids from the amino acid sequence of SEQ ID NO: 1, wherein the polypeptide comprises the 28$^{th}$ to 31$^{st}$ amino acid residue (KEKA) of amino acid sequence of SEQ ID NO: 1, or a polypeptide consisting of an amino acid sequence having 70% or more sequence homology with the polypeptide; a polynucleotide encoding the polypeptide; a pharmaceutical, cosmetic and food composition for improving alopecia and promoting hair growth comprising the polypeptide.

2 Claims, 9 Drawing Sheets

Specification includes a Sequence Listing.

(56) References Cited

OTHER PUBLICATIONS

Non-Final Office Action in corresponding U.S. Appl. No. 16/320,404, dated Jul. 13, 2020.
Final Office Action in corresponding U.S. Appl. No. 16/320,404, dated Nov. 27, 2020.
William R. Pearson, "An Introduction to Sequence Similarity ("Homology") Searching," Current Protocols in Bioinformatics 3.1.1-3, pp. 1-8, Jun. 2013.
Kumar Piyush, et al., "A Review of Benzopyran Derivatives in Pharmacotherapy of Breast Cancer," Asian Journal of Pharmaceutical and Clinical Research, vol. 11, Issue 7, 2018, pp. 43-46.

* cited by examiner 6 days after the depilation

AIMP1 PROTEIN FRAGMENT AND HAIR GROWTH-PROMOTING COMPOSITION CONTAINING SAME AS ACTIVE INGREDIENT

CROSS-REFERENCE TO RELATED PATENT APPLICATIONS

The present application is a continuation of U.S. application Ser. No. 16/320,404, filed Jan. 24, 2019, which is a is a U.S. National Phase Application under 35 U.S.C. § 371 of International Patent Application No. PCT/KR2017/008078, filed Jul. 27, 2017, and claims priority to KR 10-2016-0096256, filed Jul. 28, 2016, all of which are incorporated by reference in their entireties. The International Application was published on Feb. 1, 2018 as International Publication No. WO/2018/021839A1.

Sequence Listing

The instant application contains a Sequence Listing which has been submitted electronically in ASCII format and is hereby incorporated by reference in its entirety. Said ASCII copy, created on Jul. 16, 2019, is named 10524_007398-US0_ST5.txt and is 22.1 kilobytes in size.

Technical Field

The present invention relates to novel fragments of AIMP1 protein and a composition for improving alopecia and promoting hair growth comprising the same, more specifically it relates to a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, or a polypeptide consisting of an amino acid sequence having 70% or more sequence homology with the polypeptide; a polynucleotide encoding the polypeptide; a pharmaceutical, cosmetic and food composition for improving alopecia and promoting hair growth comprising the polypeptide.

Background Art

The present application claims priority from and the benefit of Korean Patent Application No. 10-2016-0096256 filed on Jul. 28, 2016, which is hereby incorporated by reference for all purposes as if fully set forth herein.

The pharmaceutical industry is changing from the development of natural products or chemical synthetic medications in the past to the development of protein or peptide drugs. Protein is the basic substance in the function and structure of life, and it is estimated that the protein constituting the human body is more than one million. It has been directly related to diseases and has become an important research subject for the development of therapeutic drugs. Protein or peptide drugs using them have been evaluated as innovations in pharmaceuticals because they have fewer side effects and are more effective than synthetic drugs. Currently, the importance of biomedicines in the pipeline of major pharmaceutical companies is increasing, but there are major technical problems until the launch of certain biomedicines such as peptides. Specifically, improvement of delivery technique, development of peptide with increased stability and half-life, and long-chain peptide synthesis are obstacles to commercialization. Peptides are made up of about 50 amino acids or less. It is known that to be successful as a peptide drug, it is important to find a peptide having short sequence and activity. If the peptide length is long, the synthesis cost is high and the production is not easy, and it is known that there is an absorption problem in human body.

Meanwhile, in animals including humans, hair follicles are subjected to several degeneration and regeneration processes from the time of the fetal development through the whole life. In the case of human hair growth, hair follicles continue to grow from the newborn to the adolescent period, and the hair becomes thicker and thicker. Hair follicles are composed of several types of cells, such as epithelial cells and mesenchymal cells. Mesenchymal cells act as inductive organizers of the fetal and postnatal hair follicles. Follicle germ cells are bulbar matrix cells that are responsible for most mitotic proliferation in hair follicles. During the period of generation, cells in the bulb matrix migrate upwards and proliferate and differentiate into hair matrix, inner and outer sheath cells. The hair matrix group located on the central axis of the hair follicle continues to differentiate into cells that make up the medulla, hair cortex and hair cuticle. These cells continue to move upward with keratinization of the hair cortex and cuticle cells essential for hair formation in proliferating hair follicles.

The hair cycle is divided into three stages: 1) Anagen which is active development phase during the hair follicle cycle, 2) Catagen, and 3) Telogen. The duration of each step depends on the individual age, hormonal factors, nutritional and health status, and genetic predisposition. Growth factors involved in promoting hair growth have not yet been clarified. Of the 100,000 to 150,000 scalp hairs in human adults, it is known that about 90% are in the growth phase (anagen) and the remaining 10% are in the resting phase (telogen). It is known that about 500 to 1000 hard hairs are lost every day. In humans, hair growth rate is slightly different depending on the body part, which is 0.44 mm/day for scalp hairs and 0.27 mm/day for beards or body hairs. In animals such as rats, hair cycle changes are synchronized, so that hairs of all areas are known to be in the same activity state. In rats, the first cycle of hair growth begins quickly after birth and lasts until approximately 21 days after birth. And, the second cycle starts about 35 days after birth. Previously, young rats (8 to 12 days of age) have been used as anticancer-induced alopecia models. It is known that mice treated with anticancer drugs in the first hair growth cycle totally lose hair within days. In this case, hair loss state remained unchanged until the second hair growth cycle begun. Thus, in rats, it took 20-30 days to recover from alopecia.

Hair loss or alopecia is a disease in which hair is lost. Hair loss during alopecia is not limited to scalp hair, and may occur in any part of the body. Various types of alopecia are known, including alopecia areata, androgenetic alopecia, postmenopausal alopecia, female pattern alopecia, seborrheic alopecia, alopecia pityroides, senile alopecia, cancer-induced alopecia, radiation-induced alopecia, alopecia due to trichotillomania, and postpartum alopecia, etc. The hair growth promoting therapies known to date have been reported to have limited efficacy or side effects.

Although alopecia itself does not endanger life, because it brings serious psychological stress related to appearance, it is necessary to develop a new therapeutic agent that can effectively promote hair growth, alleviate and treat alopecia safely, but have fewer side effects.

DETAILED DESCRIPTION OF THE INVENTION

Technical Problem

Accordingly, the present inventors have confirmed that a specific fragment of the AIMP1 protein exhibits excellent effect on promoting hair growth, hair loss improvement, improving and treating alopecia in vivo, thereby completing the present invention.

Therefore, an aspect of the present invention is to provide a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, or a polypeptide consisting of an amino acid sequence having 70% or more sequence homology with the polypeptide.

Another aspect of the present invention is to provide a polypeptide consisting of amino acid sequence selected from the group consisting of SEQ ID NO: 6, SEQ ID NO: 7, SEQ ID NO: 8, SEQ ID NO: 9, SEQ ID NO: 13, SEQ ID NO: 14 and SEQ ID NO: 15, or a polypeptide consisting of an amino acid sequence having 70% or more sequence homology with the polypeptide.

Another aspect of the present invention is to provide a polynucleotide encoding the polypeptide.

Another aspect of the present invention is to provide a pharmaceutical composition for promoting hair growth, promoting proliferation of hair follicle stem cells, or preventing and treating alopecia comprising one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

It is also to provide a pharmaceutical composition for promoting hair growth, promoting proliferation of hair follicle stem cells, or preventing and treating alopecia consisting of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

It is also to provide a pharmaceutical composition for promoting hair growth, promoting proliferation of hair follicle stem cells, or preventing and treating alopecia consisting essentially of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

Another aspect of the present invention is to provide the pharmaceutical composition for promoting hair growth, promoting proliferation of hair follicle stem cells, or preventing and treating alopecia, wherein the polypeptide consists of an amino acid sequence selected from the group consisting of SEQ ID NO: 6, SEQ ID NO: 7, SEQ ID NO: 8, SEQ ID NO: 9, SEQ ID NO: 13, SEQ ID NO: 14 and SEQ ID NO: 15.

Another aspect of the present invention is to provide the pharmaceutical composition for promoting hair growth, promoting proliferation of hair follicle stem cells, or preventing and treating alopecia, wherein the composition further comprises a compound or pharmaceutically acceptable salt thereof selected from the group consisting of minoxidil, cromakalin, pinacidil, naminidil, diphenylcyclopropenone, Tricomin therapeutic, cosmeceutical and pharmaceutical preparations for the prevention of hair loss and the promotion of hair growth, cyproterone acetate, danazol, flutamide; 5-alpha reductase inhibitors selected from the group consisting of finasteride, turosteride, LY-191704, MK-306 and dutasteride; s-triazines, benzopyrans, pyridinopyrans and thiane-1-oxides.

Another aspect of the present invention is to provide a cosmetic composition for promoting hair growth, or preventing and improving alopecia comprising one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

It is also to provide a cosmetic composition for promoting hair growth, or preventing and improving alopecia consisting of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

It is also to provide a cosmetic composition for promoting hair growth, or preventing and improving alopecia consisting essentially of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

Another aspect of the present invention is to provide a food composition for promoting hair growth, or preventing and improving alopecia comprising one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

It is also to provide a food composition for promoting hair growth, or preventing and improving alopecia consisting of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

It is also to provide a food composition for promoting hair growth, or preventing and improving alopecia consisting essentially of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

Another aspect of the present invention is to provide use of one or more polypeptide selected from the group consisting of a polypeptide consisting of 4 to 21 consecutive amino acids from the amino acid sequence of SEQ ID NO: 1, wherein the polypeptide comprises the 28$^{th}$ to 31$^{st}$ amino acid residue (KEKA) of amino acid sequence of SEQ ID NO: 1, and a polypeptide consisting of an amino acid sequence having 70% or more sequence homology with the polypeptide for preparing an agent for promoting hair growth, promoting proliferation of hair follicle stem cells, or preventing and treating alopecia.

Another aspect of the present invention is to provide a method for promoting hair growth, promoting proliferation of hair follicle stem cells, or preventing and treating alopecia, the method comprising administering to a subject in need thereof an effective amount of composition comprising one or more polypeptide as an active ingredient selected from the group consisting of a polypeptide consisting of 4 to 21 consecutive amino acids from the amino acid sequence of SEQ ID NO: 1, wherein the polypeptide comprises the 28$^{th}$ to 31$^{st}$ amino acid residue (KEKA) of amino acid sequence of SEQ ID NO: 1, and a polypeptide consisting of an amino acid sequence having 70% or more sequence homology with the polypeptide.

It is also to provide a method for promoting hair growth, promoting proliferation of hair follicle stem cells, or preventing and treating alopecia, the method comprising administering to a subject in need thereof an effective amount of composition consisting of one or more polypeptide as an active ingredient selected from the group consisting of a polypeptide consisting of 4 to 21 consecutive amino acids from the amino acid sequence of SEQ ID NO: 1, wherein the polypeptide comprises the 28$^{th}$ to 31$^{st}$ amino acid residue (KEKA) of amino acid sequence of SEQ ID NO: 1, and a polypeptide consisting of an amino acid sequence having 70% or more sequence homology with the polypeptide.

It is also to provide a method for promoting hair growth, promoting proliferation of hair follicle stem cells, or preventing and treating alopecia, the method comprising administering to a subject in need thereof an effective amount of composition consisting essentially of one or more polypeptide as an active ingredient selected from the group consisting of a polypeptide consisting of 4 to 21 consecutive amino acids from the amino acid sequence of SEQ ID NO: 1, wherein the polypeptide comprises the 28$^{th}$ to 31$^{st}$ amino acid residue (KEKA) of amino acid sequence of SEQ ID NO: 1, and a polypeptide consisting of an amino acid sequence having 70% or more sequence homology with the polypeptide.

Another aspect of the present invention is to provide a pharmaceutical composition for promoting hair growth, promoting proliferation of hair follicle stem cells, or preventing and treating alopecia comprising a polypeptide consisting of amino acid sequence of SEQ ID NO: 1 as an active ingredient.

It is also to provide a pharmaceutical composition for promoting hair growth, promoting proliferation of hair follicle stem cells, or preventing and treating alopecia consisting of a polypeptide consisting of amino acid sequence of SEQ ID NO: 1 as an active ingredient.

It is also to provide a pharmaceutical composition for promoting hair growth, promoting proliferation of hair follicle stem cells, or preventing and treating alopecia consisting essentially of a polypeptide consisting of amino acid sequence of SEQ ID NO: 1 as an active ingredient.

Another aspect of the present invention is to provide a cosmetic composition for promoting hair growth, or preventing and improving alopecia comprising a polypeptide consisting of amino acid sequence of SEQ ID NO: 1 as an active ingredient.

It is also to provide a cosmetic composition for promoting hair growth, or preventing and improving alopecia consisting of a polypeptide consisting of amino acid sequence of SEQ ID NO: 1 as an active ingredient.

It is also to provide a cosmetic composition for promoting hair growth, or preventing and improving alopecia consisting essentially of a polypeptide consisting of amino acid sequence of SEQ ID NO: 1 as an active ingredient.

Another aspect of the present invention is to provide a food composition for promoting hair growth, or preventing and improving alopecia comprising a polypeptide consisting of amino acid sequence of SEQ ID NO: 1 as an active ingredient.

It is also to provide a food composition for promoting hair growth, or preventing and improving alopecia consisting of a polypeptide consisting of amino acid sequence of SEQ ID NO: 1 as an active ingredient.

It is also to provide a food composition for promoting hair growth, or preventing and improving alopecia consisting essentially of a polypeptide consisting of amino acid sequence of SEQ ID NO: 1 as an active ingredient.

Another aspect of the present invention is to provide use of a polypeptide consisting of amino acid sequence of SEQ ID NO: 1 for preparing an agent for promoting hair growth, promoting proliferation of hair follicle stem cells, or preventing and treating alopecia.

Another aspect of the present invention is to provide a method for promoting hair growth, promoting proliferation of hair follicle stem cells, or preventing and treating alopecia, the method comprising administering to a subject in need thereof an effective amount of composition comprising a polypeptide consisting of amino acid sequence of SEQ ID NO: 1 as an active ingredient.

It is also to provide a method for promoting hair growth, promoting proliferation of hair follicle stem cells, or preventing and treating alopecia, the method comprising administering to a subject in need thereof an effective amount of composition consisting of a polypeptide consisting of amino acid sequence of SEQ ID NO: 1 as an active ingredient.

It is also to provide a method for promoting hair growth, promoting proliferation of hair follicle stem cells, or preventing and treating alopecia, the method comprising administering to a subject in need thereof an effective amount of composition consisting essentially of a polypeptide consisting of amino acid sequence of SEQ ID NO: 1 as an active ingredient.

Technical Solution

In accordance with an aspect of the present invention, there is provided a polypeptide consisting of 4 to 21 consecutive amino acids from the amino acid sequence of SEQ ID NO: 1, wherein the polypeptide comprises the 28$^{th}$ to 31$^{st}$ amino acid residue (KEKA) of amino acid sequence of SEQ ID NO: 1, or a polypeptide consisting of an amino acid sequence having 70% or more sequence homology with the polypeptide.

In accordance with another aspect of the present invention, there is provided a polypeptide consisting of amino acid sequence selected from the group consisting of SEQ ID NO: 6, SEQ ID NO: 7, SEQ ID NO: 8, SEQ ID NO: 9, SEQ ID NO: 13, SEQ ID NO: 14 and SEQ ID NO: 15, or a polypeptide consisting of an amino acid sequence having 70% or more sequence homology with the polypeptide.

In accordance with another aspect of the present invention, there is provided a polynucleotide encoding the polypeptide.

In accordance with another aspect of the present invention, there is provided a pharmaceutical composition for promoting hair growth, promoting proliferation of hair follicle stem cells, or preventing and treating alopecia comprising one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

There is also provided a pharmaceutical composition for promoting hair growth, promoting proliferation of hair follicle stem cells, or preventing and treating alopecia consisting of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

There is also provided a pharmaceutical composition for promoting hair growth, promoting proliferation of hair follicle stem cells, or preventing and treating alopecia consisting essentially of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

In accordance with another aspect of the present invention, there is provided the pharmaceutical composition for promoting hair growth, promoting proliferation of hair follicle stem cells, or preventing and treating alopecia, wherein the composition further comprises a compound or pharmaceutically acceptable salt thereof selected from the group consisting of minoxidil, cromakalin, pinacidil, naminidil, diphenylcyclopropenone, Tricomin therapeutic, cosmeceutical and pharmaceutical preparations for the prevention of hair loss and the promotion of hair growth, cyproterone acetate, danazol, flutamide; 5-alpha reductase inhibitors selected from the group consisting of finasteride, turosteride, LY-191704, MK-306 and dutasteride; s-triazines, benzopyrans, pyridinopyrans and thiane-1-oxides.

In accordance with another aspect of the present invention, there is provided a cosmetic composition for promoting hair growth, or preventing and improving alopecia comprising one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

There is also provided a cosmetic composition for promoting hair growth, or preventing and improving alopecia consisting of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

There is also provided a cosmetic composition for promoting hair growth, or preventing and improving alopecia consisting essentially of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

In accordance with another aspect of the present invention, there is provided a food composition for promoting hair growth, or preventing and improving alopecia comprising one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

There is also provided a food composition for promoting hair growth, or preventing and improving alopecia consisting of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

There is also provided a food composition for promoting hair growth, or preventing and improving alopecia consisting essentially of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

In accordance with another aspect of the present invention, there is provided use of one or more polypeptide selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide for preparing an agent for promoting hair growth, promoting proliferation of hair follicle stem cells, or preventing and treating alopecia.

In accordance with another aspect of the present invention, there is provided a method for promoting hair growth, promoting proliferation of hair follicle stem cells, or preventing and treating alopecia, the method comprising administering to a subject in need thereof an effective amount of composition comprising one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

There is also provided a method for promoting hair growth, promoting proliferation of hair follicle stem cells, or preventing and treating alopecia, the method comprising administering to a subject in need thereof an effective amount of composition consisting of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

There is also provided a method for promoting hair growth, promoting proliferation of hair follicle stem cells, or preventing and treating alopecia, the method comprising administering to a subject in need thereof an effective amount of composition consisting essentially of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

In accordance with another aspect of the present invention, there is provided a pharmaceutical composition for promoting hair growth, promoting proliferation of hair follicle stem cells, or preventing and treating alopecia comprising a polypeptide consisting of amino acid sequence of SEQ ID NO: 1 as an active ingredient.

There is also provided a pharmaceutical composition for promoting hair growth, promoting proliferation of hair follicle stem cells, or preventing and treating alopecia consisting of a polypeptide consisting of amino acid sequence of SEQ ID NO: 1 as an active ingredient.

There is also provided a pharmaceutical composition for promoting hair growth, promoting proliferation of hair follicle stem cells, or preventing and treating alopecia consisting essentially of a polypeptide consisting of amino acid sequence of SEQ ID NO: 1 as an active ingredient.

In accordance with another aspect of the present invention, there is provided a cosmetic composition for promoting hair growth, or preventing and improving alopecia comprising a polypeptide consisting of amino acid sequence of SEQ ID NO: 1 as an active ingredient.

There is also provided a cosmetic composition for promoting hair growth, or preventing and improving alopecia consisting of a polypeptide consisting of amino acid sequence of SEQ ID NO: 1 as an active ingredient.

There is also provided a cosmetic composition for promoting hair growth, or preventing and improving alopecia consisting essentially of a polypeptide consisting of amino acid sequence of SEQ ID NO: 1 as an active ingredient.

In accordance with another aspect of the present invention, there is provided a food composition for promoting hair growth, or preventing and improving alopecia comprising a polypeptide consisting of amino acid sequence of SEQ ID NO: 1 as an active ingredient.

There is also provided a food composition for promoting hair growth, or preventing and improving alopecia consisting of a polypeptide consisting of amino acid sequence of SEQ ID NO: 1 as an active ingredient.

There is also provided a food composition for promoting hair growth, or preventing and improving alopecia consisting essentially of a polypeptide consisting of amino acid sequence of SEQ ID NO: 1 as an active ingredient.

In accordance with another aspect of the present invention, there is provided use of a polypeptide consisting of amino acid sequence of SEQ ID NO: 1 for preparing an agent for promoting hair growth, promoting proliferation of hair follicle stem cells, or preventing and treating alopecia In accordance with another aspect of the present invention, there is provided a method for promoting hair growth, promoting proliferation of hair follicle stem cells, or preventing and treating alopecia, the method comprising administering to a subject in need thereof an effective amount of composition comprising a polypeptide consisting of amino acid sequence of SEQ ID NO: 1 as an active ingredient.

There is also provided a method for promoting hair growth, promoting proliferation of hair follicle stem cells, or preventing and treating alopecia, the method comprising administering to a subject in need thereof an effective amount of composition consisting of a polypeptide consisting of amino acid sequence of SEQ ID NO: 1 as an active ingredient.

There is also provided a method for promoting hair growth, promoting proliferation of hair follicle stem cells, or preventing and treating alopecia, the method comprising administering to a subject in need thereof an effective amount of composition consisting essentially of a polypeptide consisting of amino acid sequence of SEQ ID NO: 1 as an active ingredient.

Hereinafter, the present invention will be described in detail.

The term "KEKA residue", "KEKA sequence", or "KEKA region" in the present invention can be used interchangeably and refers to the $33^{rd}$ to $36^{th}$ amino acid region in the full length amino acid sequence of AIMP1 protein represented by SEQ ID NO: 16, SEQ ID NO: 33, SEQ ID NO: 34 or SEQ ID NO: 35. And the region corresponds to the $28^{th}$ to $31^{st}$ amino acid residue in the polypeptide of SEQ ID NO: 1 (or referred to as "Neo-Pep") which is the example of the hair growth promoting active fragment provided by the present invention.

Hereinafter, the polypeptide provided by the present invention is a fragment derived from AIMP1 protein, which comprises the $28^{th}$ to $31^{st}$ amino acid (KEKA) region in the amino acid sequence of SEQ ID NO: 1 and has remarkably excellent effect on promoting hair growth and proliferation of hair follicle stem cells. It is disclosed in the present invention for the first time that the KEKA region of AIMP1 is essential for promoting hair growth, promoting proliferation of hair follicle stem cells, preventing, improving or treating alopecia.

Therefore, the present invention provides a polypeptide consisting of 4 to 21 consecutive amino acids, preferably 10 to 21 consecutive amino acids, more preferably 15 to 20 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, or a polypeptide consisting of an amino acid sequence having 70% or more sequence homology with the polypeptide.

Preferably, the polypeptide of the present invention consists of an amino acid sequence selected from the group consisting of SEQ ID NO: 6, SEQ ID NO: 7, SEQ ID NO: 8, SEQ ID NO: 9, SEQ ID NO: 13, SEQ ID NO: 14 and SEQ ID NO: 15.

As used herein, the terms "polypeptide", "peptide" and "protein" are used interchangeably and refer to polymers of amino acid residues as commonly found in natural state proteins.

The one letter (triplet) of amino acids used herein means the following amino acids according to standard abbreviations in the biochemistry: A (Ala): alanine; C (Cys): cysteine; D (Asp): aspartic acid; E (Glu): glutamic acid; F (Phe): phenylalanine; G (Gly): glycine; H (His): histidine; I (Ile): isoleucine; K (Lys): lysine; L (Leu): leucine; M (Met): methionine; N (Asn): Asparagine; 0 (Ply): pyrrolysine; P (Pro): proline; Q (Gln): Glutamine; R (Arg): arginine; S (Ser): serine; T (Thr): threonine; U (Sec): selenocysteine, V (Val): valine; W (Trp): tryptophan; Y (Tyr): Tyrosine.

In the present invention, 'AIMP1 (ARS-interacting multifunctional protein 1) protein' was firstly known as p43 protein and was renamed as AIMP1 (Kim S H et al., Trends in Biochemical Sciences, 30: 569-574, 2005). AIMP1 binds to a multi-tRNA synthetase complex to enhance the catalytic activity of the multi-tRNA synthetase. The specific sequence of the AIMP1 protein of the present invention is not particularly limited as long as it is known in the art and can be preferably human AIMP1. Three SNPs of the AIMP1 protein are known (see NCBI SNP database): 79th alanine (Ala) in the amino acid sequence of the full-length AIMP1 (SEQ ID NO: 33 in the present specification) is substituted with proline (Pro) (SNP Accession No. rs3133166, SEQ ID NO: 16); 104th threonine (Thr) is substituted with alanine (Ala) (SNP Accession No. rs17036670, SEQ ID NO: 34); 117th threonine (Thr) is substituted with alanine (Ala) (SNP Accession No. rs2230255, SEQ ID NO: 35).

The polypeptide of the present invention, that is, polypeptide consisting of 4 to 21 consecutive amino acids from the amino acid sequence of SEQ ID NO: 1, wherein the polypeptide comprises the 28th to 31st amino acid residue (KEKA) of amino acid sequence of SEQ ID NO: 1, include functional equivalent thereof. The functional equivalent means polypeptide having at least 70% or more (70.0% to 99.9%), preferably 80% or more (80.0% to 99.9%), and more preferably 90% or more (90% to 99.9%) sequence homology (or identity) with the polypeptide of the present invention. More preferably, the functional equivalent means polypeptide having at least 70% or more, preferably 80% or more, and more preferably 90% or more sequence homology (or identity) with the polypeptide of the present invention with constant (unchanged) sequence of KEKA region (sequence). For example, these include polypeptides having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence homology, and exhibits substantially the same physiological activity as the polypeptide of the present invention. Herein, the term "substantially" means a state indicating a property of a certain property to a whole or almost the same degree. Therefore, in the present invention, "substantially the same physiological activity" means activity of promoting hair growth such as promoting the formation of hair follicle, increasing the number of hair follicle; promoting proliferation of hair follicle stem cells; or preventing, improving or treating alopecia.

Most preferably, the functional equivalent can be a polypeptide having least 70%, preferably at least 80%, more preferably at least 90% sequence homology (or identity) with the polypeptide of the present invention with the constant sequence of KEKA region (sequence) and isoelectric point (PI) of 9 to 11.

In the present invention, "homology or identity" refers to the overall relatedness between polymer molecules, such as polypeptide molecules. For example, calculation of homology/identity (%) between two polypeptide sequences can be performed by aligning two sequences for optimal comparison. Preferably, the length of the sequence arranged for comparison purposes is at least 30%, at least 40%, at least 50%, at least 60%, at least 70%, at least 80% %, at least 90%, or substantially 100% of the reference sequence. Then, the amino acids at the corresponding amino acid sites are compared with each other. If the amino acid located at the first sequence is identical to the amino acid at the corresponding site of the second sequence, the two sequences are identical at that site. The identity (%) of the two sequences is a function of the number of sites having amino acids common to the two sequences, taking into account the number and length of the gaps to be introduced for optimal alignment between the two sequences. The comparison between two sequences and the determination of identity (%) can be performed through a mathematical algorithm. For example, ClustalW (Thompson et al., 1994) can be used to measure sequence identity values using the following parameters: Pair Array Parameters—Method: Accurate, Matrix: PAM, Gap open penalty: 10.00, Gap extension penalty: 0.10; Multiple array parameters—Matrix: PAM, Gap open penalty: 10.00, delay identity: 30, penalize end gaps: on, Gap separation distance: 0, Negative Matrix: no, gap extension penalty: 0.20, residue-specific gap penalties: on, hydrophilic gap penalty: on, hydrophilic residue: GPSNDQEKR. Sequence identity in a particular residue includes the same residue that is simply derivatized.

In the present invention, the term "substantially" means a state indicating a property of a certain property to a whole or almost the same degree. The term "substantially the same" in the present invention is used related to the comparison between amino acid or nucleic acid sequences. For those of ordinary skill in the art to which the present invention pertains, two sequences will be understood to be "substantially identical" if they have identical residues at corresponding sites. As is well known in the art, amino acid or nucleic acid sequences can be compared using a variety of algorithms, for example, computer programs such as BLASTN for nucleic acid sequence comparison, BLASTP, gapped BLAST or PSI-BLAST for amino acid sequence comparison can be used. Examples of such computer programs are described in the following references: Altschul et al., Basic local alignment search tool, J. Mol. Biol., 215(3): 403-410, 1990; Altschul et al., Methods in Enzymology; Altschul et al., Nucleic Acids Res. 25:3389-3402, 1997; Baxevanis 외, Bioinformatics: A Practical Guide to the Analysis of Genes and Proteins, Wiley, 1998; 및 Misener et al., (eds.), Bioinformatics Methods and Protocols (Methods in Molecular Biology, Vol. 132), Humana Press, 1999. In addition to searching for the same sequence, the computer programs described above typically provide a degree of identity. In two sequences, it is considered to be "substantially the same" sequences if at least 70%, preferably at least 80%, at least 85%, at least 90%, at least 91%, at least 92%, at least 93%, at least 94%, at least 95%, at least 96%, at least 97%, at least 98%, at least 99% or more of the residue at the corresponding site over a certain length of residue is identical. Preferably, the "certain length of residue" can be a residue of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, 100, 105, 110, 115, 120, 125, 130, 135, 140, 145, 150, 155, 160, 165, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more.

In the present invention, the term "corresponding" is often used to determine the position/identity of the amino acid residues of a given polypeptide. As is conventional, residues in a polypeptide are often designated using a canonical numbering system based on reference-related polypeptides. Thus, for example, a "corresponding" amino acid in the residue at the 190th position doesn't always have to be at the 190th position in a particular amino acid chain, and one of ordinary skill in the art will readily understand how to identify the "corresponding" amino acid.

The "functional equivalent" can be a polypeptide that is produced as a result of addition, substitution or deletion of some amino acid sequence of the polypeptide of the present invention. The substitution of the amino acid is preferably a conservative substitution. Examples of conservative substitutions of amino acids present in nature are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur containing amino acids (Cys, Met). Also included in the functional equivalent is variant in which a portion of the amino acid is deleted in the amino acid sequence of the polypeptide of the present invention. The deletion or substitution of the amino acid is preferably located in a region that is not directly related to the physiological activity of the polypeptide of the present invention. In the present invention, the region directly related to the physiological activity is a KEKA region, and the deletion or substitution can be located at a region other than the above-mentioned region. Also included are variants in which some amino acids are added at both ends or in the sequence of the amino acid of the polypeptide of the present invention. Also included in the functional equivalent of the present invention is protein or polypeptide derivatives in which some of the chemical structures of the proteins are modified while maintaining the basic skeleton and physiological activity of the protein according to the present invention. This includes, for example, structural modifications to alter the stability, shelf stability, volatility or solubility of the protein of the present invention.

In the present invention, sequence homology and identity are defined as the percentage of amino acid residues of the candidate sequence relative to the amino acid sequence of the polypeptide of the present invention after aligning the candidate sequence with the amino acid sequence of the polypeptide of the present invention and introducing a gap. If necessary, conservative substitutions as part of sequence homology are not considered to obtain maximum percent sequence homology. Also, the N-terminal, C-terminal or internal stretch, deletion or insertion of an amino acid sequence of a polypeptide of the invention is not interpreted as a sequence that affects sequence homology or identity. In addition, the sequence homology can be determined by standard methods used to compare similar region of amino acid sequences of two proteins or polypeptides. BLAST or such a computer program aligns two proteins or polypeptides so that each amino acid is optimally matched (along the full length sequence of one or two sequences or along the predicted region of one or two sequences). The program provides default opening penalty and default gap penalty, and provides scoring matrix such as a PAM250 (Standard Scoring Matrix; Dayhoff et al., In Atlas of Protein Sequence & lt; RTI ID=0.0 & gt; Structure, vol 5, supp 3, 1978). For example, percentage homogeneity can be calculated as follows: After multiplying the total number of identical matches by 100 and dividing by the sum of the length of a longer sequence in a matched span and the number of gaps that is introduced into the longer sequence to align the two sequences.

The polypeptides of the present invention can be constructed by genetic engineering methods. First, a polynucleotide sequence encoding the polypeptide of the present invention is constructed according to a conventional method. The polynucleotide sequence can be constructed, for example, by PCR amplification of a polynucleotide encoding the human AIMP1 gene as a template using an appropriate primer. Alternatively, DNA sequences may be synthesized by standard methods known in the art, for example, using an automated DNA synthesizer (commercially available from Biosearch or Applied Biosystems Inc). The constructed polynucleotide is then inserted into a vector comprising one or more expression control sequence (e.g., promoters, enhancers, etc.) which is operatively linked with the polynucleotide so that controls the expression of base sequence of the polynucleotide, followed by transform host cells with the recombinant expression vector. The resulting transgenic cells are cultured under a medium and conditions suitable for the expression of the DNA sequence, and collect substantially pure protein encoded by the DNA sequence from the culture. The collection means separating (isolating) and/or purifying the objective peptide using methods known in the art (e.g. chromatography).

The term "substantially pure polypeptide or protein" means substantially free of any other protein derived from the host cells. Genetic engineering methods for protein synthesis of the present invention can be found in the following references: Maniatis et al., Molecular Cloning; A laboratory Manual, Cold Spring Harbor laboratory, 1982; Sambrook et al., supra; Gene Expression Technology, Method in Enzymology, Genetics and Molecular Biology, Method in Enzymology, Guthrie & Fink (eds.), Academic Press, San Diego, Calif., 1991; and Hitzeman et al., J. Biol. Chem., 255:12073-12080, 1990.

The polypeptides of the present invention can also be chemically synthesized by techniques known in the art (Creighton, Proteins: Structures and Molecular Principles, WH Freeman and Co., NY (1983)). That is, the polypeptides of the present invention can be prepared using conventional stepwise liquid or solid phase synthesis, fractional condensation, F-MOC or T-BOC chemistry (Chemical Approaches to the Synthesis of Peptides and Proteins, Williams et al., Eds., CRC Press, Boca Raton Fla., (1997); A Practical Approach, Atherton & Sheppard, Eds., IRL Press, Oxford, England, (1989)). A preferred method of preparation is solid phase synthesis. The polypeptide of the present invention can be synthesized by a condensation reaction between protected amino acids in a conventional solid-phase method, sequentially proceeding according to the amino acid sequence identified starting from the C-terminal. After the condensation reaction, the protecting group and the carrier to which the C-terminal amino acid is linked can be removed by a known method such as acid decomposition or aminolysis. The above-mentioned peptide synthesis methods are described in detail in the relevant book (Gross and Meienhofer's, The Peptides, vol 2, Academic Press, 1980).

The protein produced by the genetic engineering method or the chemically synthesized protein can be separated and purified by various methods known in the art such as extraction, recrystallization, various chromatography (gel filtration, ion exchange, precipitation, adsorption, reverse phase), electrophoresis, counter current distribution method, etc.

In addition, the present invention provides a polynucleotide encoding the polypeptide of the present invention, that is a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1. The polynucleotide is not particularly limited in its basic constitution as long as it encodes the above-mentioned polypeptide of the present invention. Preferably, the polynucleotide encoding the polypeptide of the invention consists of nucleotide sequence selected from the group consisting of SEQ ID NO: 22 (encoding the N5 polypeptide of SEQ ID NO: 6), SEQ ID NO: 23 (encoding the N6 polypeptide of SEQ ID NO: 7), SEQ ID NO: 24 (encoding the N7 polypeptide of SEQ ID NO: 8), SEQ ID NO: 25 (encoding the N8 polypeptide of SEQ ID NO: 9), SEQ ID NO: 29 (encoding the N12 polypeptide of SEQ ID NO: 13), SEQ ID NO: 30 (encoding the N13 polypeptide of SEQ ID NO: 14) and SEQ ID NO: 31 (encoding the N14 polypeptide of SEQ ID NO: 15).

In the present invention, "polynucleotide", "nucleic acid" refers to a deoxyribonucleotide (DNA) or a ribonucleotide (RNA) in the form of a single-stranded or double-stranded nucleic acid. Unless otherwise limited, it also includes known analogs of natural nucleotides that hybridize to nucleic acids in a manner similar to naturally occurring nucleotides.

In addition, the present invention provides a pharmaceutical composition for promoting hair growth, promoting proliferation of hair follicle stem cells, or preventing and treating alopecia comprising one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

The present invention also provides a pharmaceutical composition for promoting hair growth, promoting proliferation of hair follicle stem cells, or preventing and treating alopecia consisting of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

The present invention also provides a pharmaceutical composition for promoting hair growth, promoting proliferation of hair follicle stem cells, or preventing and treating alopecia consisting essentially of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

Preferably, in the pharmaceutical composition of the present invention, the polypeptide can be a polypeptide consisting of an amino acid sequence selected from the group consisting of SEQ ID NO: 6, SEQ ID NO: 7, SEQ ID NO: 8, SEQ ID NO: 9, SEQ ID NO: 13, SEQ ID NO: 14 and SEQ ID NO: 15.

In addition, the present invention provides a pharmaceutical composition for promoting hair growth, promoting proliferation of hair follicle stem cells, or preventing and treating alopecia comprising a polypeptide consisting of amino acid sequence of SEQ ID NO: 1 as an active ingredient.

The present invention also provides a pharmaceutical composition for promoting hair growth, promoting proliferation of hair follicle stem cells, or preventing and treating alopecia consisting of a polypeptide consisting of amino acid sequence of SEQ ID NO: 1 as an active ingredient.

The present invention also provides a pharmaceutical composition for promoting hair growth, promoting proliferation of hair follicle stem cells, or preventing and treating alopecia consisting essentially of a polypeptide consisting of amino acid sequence of SEQ ID NO: 1 as an active ingredient.

In the present invention, the term "hair" refers to scalp hair, hair, facial hair and/or body hair, which broadly includes scalp hair, eyelashes, eyebrows, mustache, beard, ear hair, nose hair, chest hair, pubic hair, assistant hair, and the likes, but is not limited thereto.

In the present invention, the term "promoting hair growth" includes promoting hair production and growth in the hair follicle as well as promoting the growth of existing hair, and includes promoting hair follicle formation, structural stabilization of hair follicles and facilitating nutrient and oxygen supply, faster induction of anagen phase and/or prolongation of the main anagen phase (growth phase) of hair cycle and/or increase in hair growth rate and/or increase in width of hair, and this includes, but is not limited to, induction or improvement of hair growth and making it more visible to the eye.

In the present invention, "hair loss or alopecia" is used to mean all the symptoms of hair loss, regardless of the specific biological mechanism of hair loss. As used herein, "preventing and treating alopecia" is used broadly to refer to prevention, improvement, and treatment of alopecia.

The polypeptide according to the invention can be used as itself or in the form of a salt, preferably a pharmaceutically acceptable salt. The term "pharmaceutically acceptable" as used herein means physiologically acceptable, does not inhibit the action of the active ingredient when administered to humans, and does not usually cause an allergic reaction such as gastrointestinal disorder, dizziness or similar side effects. As the salt, an acid addition salt formed by a pharmaceutically acceptable free acid is preferable, and as the free acid, organic acid and inorganic acid can be used. The organic acids include, but are not limited to, citric acid, acetic acid, lactic acid, tartaric acid, maleic acid, fumaric acid, formic acid, propionic acid, oxalic acid, trifluoracetic acid, benzoic acid, gluconic acid, methosulfonic acid, glycolic acid, succinic acid, 4-toluensulfonic acid, glutamic acid and aspartic acid. The inorganic acid includes, but is not limited to, hydrochloric acid, bromic acid, sulfuric acid, and phosphoric acid.

The pharmaceutical composition of the present invention can be variously formulated according to the route of administration by a method known in the art together with a pharmaceutically acceptable carrier for promoting hair growth promoting and/or preventing and treating alopecia. The carriers include all types of solvents, dispersion media, oil-in-water or water-in-oil emulsions, aqueous compositions, liposomes, microbeads and microsomes.

The route of administration can be oral or parenteral. The parenteral administration methods include, but are not limited to, intravenous, intramuscular, intraarterial, intramedullary, intrathecal, intracardiac, transdermal, subcutaneous, intraperitoneal, intranasal, enteral, topical, sublingual or rectal administration.

When the pharmaceutical composition of the present invention is to be orally administered, the pharmaceutical composition of the present invention can be formulated into various types such as powder, granule, tablet, pill, sugar, capsule, liquid, gel, syrup, suspension, wafer, and the like. Examples of suitable carriers include saccharides including lactose, dextrose, sucrose, sorbitol, mannitol, xylitol, erythritol and maltitol, and starches including corn starch, wheat starch, rice starch and potato starch, and cellulose such as cellulose, methyl cellulose, sodium carboxymethyl cellulose and hydroxypropylmethyl cellulose, and fillers such as gelatin, polyvinyl pyrrolidone and the like. In addition, cross-linked polyvinylpyrrolidone, agar, alginic acid or sodium alginate may optionally be added as a disintegrant. Furthermore, the pharmaceutical composition can further comprise an anti-coagulant, a lubricant, a wetting agent, a flavoring agent, an emulsifying agent and an antiseptic agent.

In addition, when administered parenterally, the pharmaceutical composition of the present invention can be formulated in accordance with methods known in the art in the form of injections, transdermal drugs, and nasal inhalers together with suitable non-oral carriers. In the case of the injections, they must be sterilized and protected from contamination of microorganisms such as bacteria and fungi. Examples of suitable carriers for injections include, but are not limited to, solvents or dispersion media containing water, ethanol, polyols (such as glycerol, propylene glycol and liquid polyethylene glycol, etc.), mixtures thereof and/or vegetable oils. More preferably, suitable carriers include, but are not limited to, Hank's solution, Ringer's solution, phosphate buffered saline (PBS) containing triethanolamine or isotonic solutions such as sterile water for injection, 10% ethanol, 40% propylene glycol and 5% dextrose. In order to protect the injections from microbial contamination, various antibacterial and antifungal agents such as parabens, chlorobutanol, phenol, sorbic acid, thimerosal and the like may be further included. In addition, the injections can in most cases further comprise an isotonic agent such as sugar or sodium chloride.

Examples of transdermal administration forms include ointments, creams, lotions, gels, solutions for external use, pastes, liniments, and air rolls. In the above, transdermal administration means that the pharmaceutical composition is locally administered to the skin, whereby an effective amount of the active ingredient contained in the pharmaceutical composition is delivered into the skin. For example, the pharmaceutical composition of the present invention can be prepared into a injectable formulation, which may be administered by pricking the skin lightly with a 30-gauge thin injection needle or by directly applying it to the skin. These formulations are described in a commonly known formulary article in pharmaceutical chemistry (Remington's Pharmaceutical Science, 15th Edition, 1975, Mack Publishing Company, Easton, Pa.).

In the case of an inhalation administration form, the polypeptide used in accordance with the present invention can be conveniently delivered in the form of aerosol spray from pressurized pack or a fog machine using a suitable propellant, such as dichlorofluoromethane, trichlorofluoromethane, dichlorotetrafluoroethane, carbon dioxide or other suitable gases. In the case of a pressurized aerosol, the dosage unit may be determined by providing a valve that delivers a metered amount. For example, gelatin capsules and cartridges for use in an inhaler or insufflator can be formulated to contain a compound and a powder mix of a suitable powder base such as lactose or starch.

As other pharmaceutically acceptable carriers, reference may be made to those described in the following references (Remington's Pharmaceutical Sciences, 19th ed., Mack Publishing Company, Easton, Pa., 1995).

The pharmaceutical composition according to the present invention can also contain one or more buffers (e.g., saline or PBS), a carbohydrate (e.g., glucose, mannose, sucrose or dextran), an antioxidant, a bacteriostatic, (e.g., EDTA or glutathione), an adjuvant (e.g., aluminum hydroxide), a suspending agent, a thickening agent and/or a preservative.

In addition, the pharmaceutical compositions of the present invention can be formulated using methods known in the art so as to provide rapid, sustained or delayed release of the active ingredient after administration to mammals.

In addition, the pharmaceutical composition of the present invention can be administered alone or in combination with a known compound having alopecia prevention or hair growth promoting effect. Such combination therapies include the methods of being included in the same composition or administered simultaneously, and include administering the polypeptide of the present invention at least once in the process of a treatment using one or more other alopecia treatment/hair growth promoters, but is not limited thereto.

By "administration form" or "single administration form" herein is meant a physically discrete unit of the therapeutic protein for the patient to be treated. Each treatment unit contains a pre-measured amount of active material to provide the desired therapeutic effect. However, the total dosage of the therapeutic composition is determined by the attending physician within sufficient medical judgment.

Examples of a known compound having a alopecia prevention or hair growth promoting effect that can be further used in combination with the polypeptide of the present invention or a pharmaceutical composition comprising the polypeptide of the present invention include compounds or pharmaceutically acceptable salts thereof selected from the group consisting of minoxidil, cromakalin, pinacidil, naminidil, diphenylcyclopropenone, Tricomin therapeutic, cosmeceutical and pharmaceutical preparations for the prevention of hair loss and the promotion of hair growth, cyproterone acetate, danazol, flutamide; 5-alpha reductase inhibitors selected from the group consisting of finasteride, turosteride, LY-191704, MK-306 and dutasteride; s-triazines, benzopyrans, pyridinopyrans and thiane-1-oxides, but not limited thereto.

In addition, the present invention provides a cosmetic composition for promoting hair growth, or preventing and improving alopecia comprising one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

The present invention also provides a cosmetic composition for promoting hair growth, or preventing and improving alopecia consisting of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

The present invention also provides a cosmetic composition for promoting hair growth, or preventing and improving alopecia consisting essentially of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

Preferably, in the cosmetic composition of the present invention, the polypeptide can be a polypeptide consisting of an amino acid sequence selected from the group consisting of SEQ ID NO: 6, SEQ ID NO: 7, SEQ ID NO: 8, SEQ ID NO: 9, SEQ ID NO: 13, SEQ ID NO: 14 and SEQ ID NO: 15.

In addition, the present invention provides a cosmetic composition for promoting hair growth, or preventing and improving alopecia comprising a polypeptide consisting of amino acid sequence of SEQ ID NO: 1 as an active ingredient.

The present invention also provides a cosmetic composition for promoting hair growth, or preventing and improving alopecia consisting of a polypeptide consisting of amino acid sequence of SEQ ID NO: 1 as an active ingredient.

The present invention also provides a cosmetic composition for promoting hair growth, or preventing and improving alopecia consisting essentially of a polypeptide consisting of amino acid sequence of SEQ ID NO: 1 as an active ingredient.

The cosmetic composition of the present invention can be prepared in any formulation conventionally produced in the art, and it is also possible to use a dermatologically acceptable medium or base in addition to the polypeptide of the present invention, so that it can be prepared in the form of topical or systemic adjuvant that is commonly used in the dermatological field.

The cosmetic composition of the present invention can further comprises adjuvant commonly used in the cosmetic or dermatology field, in addition to the polypeptide according to the present invention, such as a lipid, an organic solvent, a solubilizing agent, a thickening agent and a gelling agent, a softening agent, an antioxidant, a suspending agent, a stabilizer, a foaming agent, a perfuming agent, a surfactant, water, ionic or nonionic emulsifiers, a filler, a sequestrant and chelating agent, a preservative, a vitamin, a blocking agent, a wetting agent, an essential oil, a dye, a pigment, a hydrophilic or lipophilic active agent, a lipid vesicle or a any other ingredient used in cosmetics or dermatology. And the above ingredients can be added in amounts commonly used in the field of dermatology.

Formulations of suitable cosmetic compositions include, for example, solutions, gels, solid or kneaded anhydrous products, emulsions obtained by dispersing the oil phase in water, suspensions, microemulsions, microcapsules, microgranules or ionic (liposomes), form of a follicular dispersion, cream, skin, lotion, powder, ointment, spray or conceal stick. It can also be prepared in the form of a foam or an aerosol composition further containing a compressed propellant. Examples of the cosmetic preparation to which the cosmetic composition of the present invention can be added include, but are not limited to, skin lotion, skin softener, skin toner, convergent lotion, softening lotion, nutritional lotion, astringent, lotion, milk lotion, moisturizing lotion, nourishing lotion, body cream, massage cream, nourishing cream, moisture cream, hand cream, essence, nourishing essence, pack, soap, shampoo, cleansing foam, cleansing lotion, cleansing Cream, body lotion, body cleanser, treatment, serum, milk, press powder, loose powder, eye shadow, and the like.

The content of the polypeptide of the present invention contained in the cosmetic composition of the present invention can be in the range of 0.0001 to 50% by weight, preferably 0.01 to 10% by weight based on the total weight of the cosmetic composition.

In addition, the present invention provides a food composition for promoting hair growth, or preventing and improving alopecia comprising one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

The present invention also provides a food composition for promoting hair growth, or preventing and improving alopecia consisting of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

The present invention also provides a food composition for promoting hair growth, or preventing and improving alopecia consisting essentially of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

Preferably, in the food composition of the present invention, the polypeptide can be a polypeptide consisting of an amino acid sequence selected from the group consisting of SEQ ID NO: 6, SEQ ID NO: 7, SEQ ID NO: 8, SEQ ID NO: 9, SEQ ID NO: 13, SEQ ID NO: 14 and SEQ ID NO: 15.

In addition, the present invention provides a food composition for promoting hair growth, or preventing and improving alopecia comprising a polypeptide consisting of amino acid sequence of SEQ ID NO: 1 as an active ingredient.

The present invention also provides a food composition for promoting hair growth, or preventing and improving alopecia consisting of a polypeptide consisting of amino acid sequence of SEQ ID NO: 1 as an active ingredient.

The present invention also provides a food composition for promoting hair growth, or preventing and improving alopecia consisting essentially of a polypeptide consisting of amino acid sequence of SEQ ID NO: 1 as an active ingredient.

The food composition of the present invention includes all forms such as functional food, nutritional supplement, health food and food additives. These types can be prepared in various forms according to conventional methods known in the art. For example, as the health food, the food composition itself of the present invention can be prepared in the form of tea, juice, and drink, and can be ingested as granulated, encapsulated, and powdered form. In addition, the food composition of the present invention can be prepared in the form of a composition by mixing with a known substance or active ingredient known to have the effect of promoting hair growth, or preventing or improving alopecia. In addition, the functional foods also include beverages (including alcoholic beverages), fruits and their processed foods (e.g., canned fruits, bottled, jam, marmalade, etc.), fish, meats and processed foods (e.g., ham, etc.), breads and noodles (e.g., udon, buckwheat noodles, ramen noodles, spaghetti, macaroni, etc.), juice, various drinks, cookies, yeot, dairy products (e.g., butter, cheeses, etc.), edible plant oils, margarine, vegetable protein, retort food, frozen food, various kinds of seasoning (e.g., soybean paste, soy sauce, sauce, etc.).

The preferred content of the food composition of the polypeptide of the present invention is not particularly limited, but is preferably 0.01 to 50% by weight in the finally prepared food. In order to use the food composition of the present invention in the form of a food additive, it can be prepared in the form of powder or concentrate.

In addition, the present invention provides use of one or more polypeptide selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide for preparing an agent for promoting hair growth, promoting proliferation of hair follicle stem cells, or preventing and treating alopecia.

In addition, the present invention provides a method for promoting hair growth, promoting proliferation of hair follicle stem cells, or preventing and treating alopecia, the method comprising administering to a subject in need thereof an effective amount of composition comprising one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

The present invention also provides a method for promoting hair growth, promoting proliferation of hair follicle stem cells, or preventing and treating alopecia, the method comprising administering to a subject in need thereof an effective amount of composition consisting of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

The present invention also provides a method for promoting hair growth, promoting proliferation of hair follicle stem cells, or preventing and treating alopecia, the method comprising administering to a subject in need thereof an effective amount of composition consisting essentially of one or more polypeptide as an active ingredient selected from the group consisting of a polypeptide consisting of 4 to 21 consecutive amino acids from the amino acid sequence of SEQ ID NO: 1, wherein the polypeptide comprises the $28^{th}$ to $31^{st}$ amino acid residue (KEKA) of amino acid sequence of SEQ ID NO: 1, and a polypeptide consisting of an amino acid sequence having 70% or more sequence homology with the polypeptide.

In addition, the present invention provides use of a polypeptide consisting of amino acid sequence of SEQ ID NO: 1 for preparing an agent for promoting hair growth, promoting proliferation of hair follicle stem cells, or preventing and treating alopecia.

In addition, the present invention provides a method for promoting hair growth, promoting proliferation of hair follicle stem cells, or preventing and treating alopecia, the method comprising administering to a subject in need thereof an effective amount of composition comprising a polypeptide consisting of amino acid sequence of SEQ ID NO: 1 as an active ingredient.

The present invention provides a method for promoting hair growth, promoting proliferation of hair follicle stem cells, or preventing and treating alopecia, the method comprising administering to a subject in need thereof an effective amount of composition consisting of a polypeptide consisting of amino acid sequence of SEQ ID NO: 1 as an active ingredient.

The present invention provides a method for promoting hair growth, promoting proliferation of hair follicle stem cells, or preventing and treating alopecia, the method comprising administering to a subject in need thereof an effective amount of composition consisting essentially of a polypeptide consisting of amino acid sequence of SEQ ID NO: 1 as an active ingredient.

The "effective amount" of the present invention refers to an amount that, when administered to an individual, represents an improvement, treatment, or prevention effect of alopecia and effect of promoting hair growth, and the "individual" includes an animal, preferably a mammal, in particular may be an animal comprising human, an animal-derived cell, tissue, organs, and the like. The subject can be a patient requiring the effect.

The 'preparation or composition' of the present invention can be in the form of a food composition, a cosmetic composition, a pharmaceutical composition, and the like, as described above.

The term "comprising" of the present invention is used synonymously with "containing" or "characterized in that" and does not exclude additional component elements or method steps not mentioned in the composition or method. The term "consisting of" refers to exclude additional elements, steps or components not otherwise mentioned. The term "consisting essentially of" is intended to encompass component elements or steps, etc., which, in addition to the described component elements or steps, do not substantially affect their underlying properties.

Advantageous Effects

Accordingly, the present invention provides a novel fragment of AIMP1 protein and a composition comprising the same as an active ingredient for promoting hair growth, or preventing, improving and treating alopecia. The novel polypeptide according to the present invention and the composition comprising the same as an active ingredient can be used for improving and preventing alopecia, and promoting hair growth, because it enhances hair growth.

MODE FOR CARRYING OUT THE INVENTION

Figure 1:
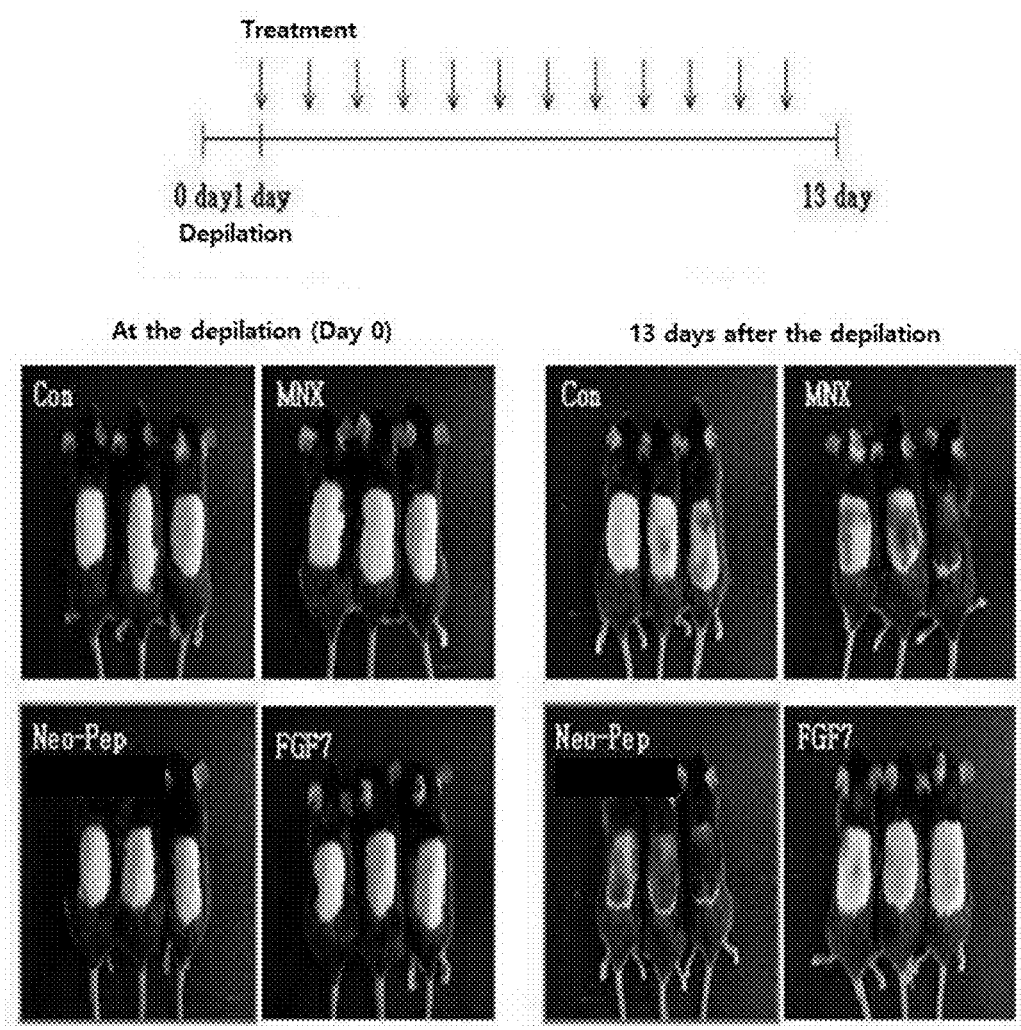
In FIG. 1, the upper part of the figure shows an outline of a mouse experiment for confirming the in vivo hair growth promoting effect of the polypeptide of the present invention, and the lower part of the figure shows a state in which hair of a dorsal skin of the mouse is removed before the beginning of the experiment (Day 0, left panel), and about two weeks later in which hair of the dorsal skin of the mouse grew (Day 13, right panel) [Control (Con): 20% Glycerol/PBS; 3% Minoxidil (MNX, 140 mM); Neo-Pep polypeptide (polypeptide of SEQ ID NO: 1, 100 nM); FGF7 (100 nM)].

Hereinafter, the present invention will be described in detail.

However, the following examples are merely for illustrating the present invention and are not intended to limit the scope of the present invention.

Method

1. In Vivo Study

The hair of the dorsal skin of mice (7 weeks old male C57BL6, purchased from Orient Bio Inc.) was cut out with a clipper, and hair removal cream (Niclean, Ildong Pharmaceutical) was applied. The depilated area was about 2×2.5 cm. Mice were treated with 20% glycerol/PBS (control group), 3% Minoxidil (MNX, 140 mM), FGF7 (100 nM) or Neo-Pep of the present invention (polypeptide of SEQ ID NO: 1, 100 nM), respectively, once a day in 80 µl using brush, for 13 days (n=6 per group).

2. Hematoxylin-Eosin (H&E) Staining

Skin samples of 7 weeks old male C57BL6 mice (purchased from Orient Bio Inc.) were collected and placed in a cryomold using an OCT compound (Tissue-Tek) and stored at −80° C. in a freezer. After tissue sections were prepared with Microm HM 525 (Thermo Scientific), the tissue sections prepared in the slide glass were fixed with 4% paraformaldehyde for 10 minutes, washed twice with PBS for 5 minutes, and then stained with 50 µl of hematoxylin solution (Sigma Aldrich) for 6 minutes and washed with water and PBS for 5 minutes. Then, stained with eosin (Sigma Aldrich), briefly washed with water and washed with PBS for 5 min, then briefly twice with 95% ethanol and 100% ethanol, respectively. After treatment with xylene (Duksan) twice for 2 min, the stained tissue sections were covered with cover slides and fixed.

3. Separation of CD34+ Cells for Proliferation Assay

The hair of the dorsal skin of 7 weeks old male C57BL6 mice (purchased from Orient Bio Inc.) were cut with a clipper and skin tissue samples of the depilated dorsal region of the mice were collected. The collected skin tissue samples were immersed in medium using collagenase, DNase I, and hyaluronidase, and cells were isolated using Gentle MAC-STM Dissociator (Miltenyi Biotec). After the cells were separated, the separated cells were incubated with a mouse CD34-Biotin antibody (Miltenyi Biotec). Cells and antibody solutions were incubated with streptavidin microbeads (Miltenyi Biotec) and then separated using LS column (Miltenyi Biotec). The separated cells were cultured in DMEM medium containing 10% FBS, 1% penicillin/streptomycin solution in humidified air of 95% 02 and 5% CO2 at 37° C.

4. BrdU Proliferation Assay

Cell proliferation can be confirmed using the BrdU cell proliferation assay kit (Cell Signaling). Proliferation assays were performed using protocols presented by Miltenyi Biotec. Briefly, the cells were incubated with BrdU for 2 h. The primary BrdU detection antibody was incubated for 1 hour and the secondary anti-mouse IgG, HRP-conjugate antibody was incubated for 30 minutes.

5. In Vitro Hair Growth Assay and Observation of mRNA Expression Level

A hair growth in vitro assay was performed using the Cyquant Assay (Thermo Fisher). The assay conditions were as follows: Cell—CD34+ hair follicle stem cells; Culture plate—96 well plate; Cell number—$3\times10^3$ cells/well; Concentration of final polypeptide—100 nM; incubation time 24 hours.

In order to confirm the induction of CD34+ hair follicle stem cell proliferation through β-catenin pathway, mRNA expression levels of β-catenin target genes AXIN, CD44 and TCF7 were confirmed by the following method. Specifically, each test substance was treated and CD34+ cells were cultured for 8 hours. Then, the cultured cells were collected, RNA was isolated using GeneJET RNA purification kit (Thermo Fisher, K0731), and cDNA was synthesized with the Maxima first strand cDNA synthesis kit (Thermo Fisher, K1642). qRT-PCR was performed using each of the gene-specific primers (TCF7: 5'-ATCCTTGATGCTGGGAT-TCTG-3' (SEQ ID NO: 36) and 5'-CTTCTCTTGCCTTGGGTTCTG-3' (SEQ ID NO: 37), AXIN2: 5'-CTCCTTGGAGGCAAGAGC-3' (SEQ ID NO: 38) and 5'-GGCCACGCAGCACCGCTG-3' (SEQ ID NO: 39), CD44: 5'-CCACAGCCTCCTTTCAATAACC-3' (SEQ ID NO: 40) and 5'-GGAGTCTTCGCTTGGGGTA-3' (SEQ ID NO: 41)), Maxima SYBR green/ROX qPCR master mix (Thermo Fisher, K0222) and 7500 Real-time PCR system (Applied Biosystems, 2720; condition: 40 cycles, 2 step (95° C. for 15 sec, and 54° C. for 60 sec). The expression level of each gene was calculated by the $\Delta\Delta C_T$ method.

6. Histological Analysis

A skin sample of 7 weeks old male C57BL6 mice (purchased from Orient Bio Inc.) was collected and placed in a paraffin block. IHC (Immunohistochemistry) was performed using Cytokeratin 15 antibody (Abcam), BrdU antibody (Novusbio), and β-catenin antibody.

For reference, β-catenin is a hair follicle signaling marker, Cytokeratin 15 is a hair follicle stem cell marker, and BrdU is a cell proliferation marker.

Example 1: Hair Growth Promoting Effect of the Polypeptide of the Present Invention The effects of the polypeptide according to the present invention in promoting hair growth and preventing or treating alopecia in vivo were confirmed using mice. The hair was removed from the dorsal skin of the mice, and the hair regrowth pattern after treatment with the polypeptide according to the present invention was compared with the control group (see FIG. 1).

Specifically, the hair of the dorsal skin of a mouse (7 weeks old male C57BL6, purchased from Orient Bio Inc.) was cut out with a clipper, and hair removal cream (Niclean, Ildong Pharmaceutical) was applied. The depilated area was about 2×2.5 cm. Mice were treated with 20% glycerol/PBS (control group), 3% Minoxidil (MNX, 140 mM), FGF7 (100 nM) or Neo-Pep of the present invention (polypeptide of SEQ ID NO: 1, 100 nM), respectively, once a day in 80 μl using brush, for 13 days (n=6 per group). For comparative observation, the dorsal skin of the mouse was photographed before and after the beginning of the test.

As can be seen from the images of the skin of the mice at the bottom of FIG. 1, 13 days after depilation of dorsal skin, the dorsal hair of the mice treated with the polypeptide of the present invention "Neo-Pep" (polypeptide of SEQ ID NO: 1) grew much more than that of control and other experimental groups (i.e., MNX and FGF7).

In addition, dorsal skin samples of the mice were collected and placed in a cryomold using an OCT compound (Tissue-Tek) and stored at −80° C. in a freezer. After tissue sections were prepared with Microm HM 525 (Thermo Scientific), the tissue sections prepared in the slide glass were fixed with 4% paraformaldehyde for 10 minutes, washed twice with PBS for 5 minutes, and then stained with 50 μl of hematoxylin solution (Sigma Aldrich) for 6 minutes and washed with water and PBS for 5 minutes. Then, stained with eosin (Sigma Aldrich), briefly washed with water and washed with PBS for 5 min, then briefly twice with 95% ethanol and 100% ethanol, respectively. After treatment with xylene (Duksan) twice for 2 min, the stained tissue sections were covered with cover slides and fixed. The number of hair follicles of anagen phase (growth phase) was counted and compared quantitatively in dorsal skin sections of each group stained with hematoxylin and eosin (H & E).

Figure 2:
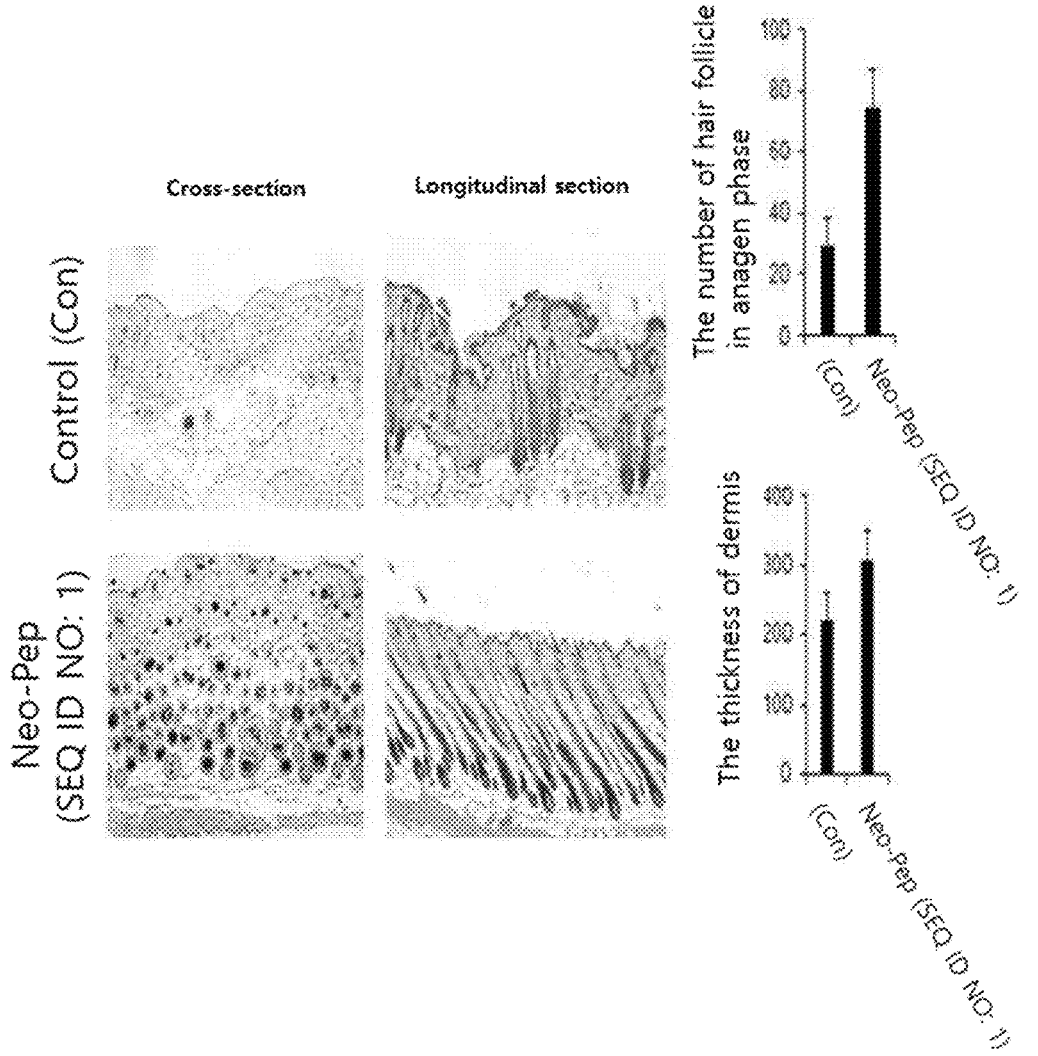
In FIG. 2, in the left part of the figure, the cross-sectional and longitudinal section images of the skin tissue and the hair follicle region observed through a phase contrast microscope are shown in order to compare the hair growth in the control group and the Neo-Pep polypeptide (polypeptide of SEQ ID NO: 1) treated group at Day 13 after depilation, and the right part of the figure shows a graph comparing the number of hair follicle cell in anagen phase and the thickness of the dermis quantitatively.

As shown in FIG. 2, as a result of comparing the number of hair follicles of anagen phase in the mouse skin sections stained with H & E, in the dorsal skin of the mice treated with the polypeptide of the present invention "Neo-Pep" (polypeptide of SEQ ID NO: 1), more than twice as much hair follicles of anagen phase were observed as compared with the control (Con), and the dermis thickness was also much thicker.

Through the test result, it was confirmed that the polypeptide of the present invention "Neo-Pep" (SEQ ID NO: 1) has effect on promoting hair growth, and improving and treating alopecia in vivo.

Figure 3:
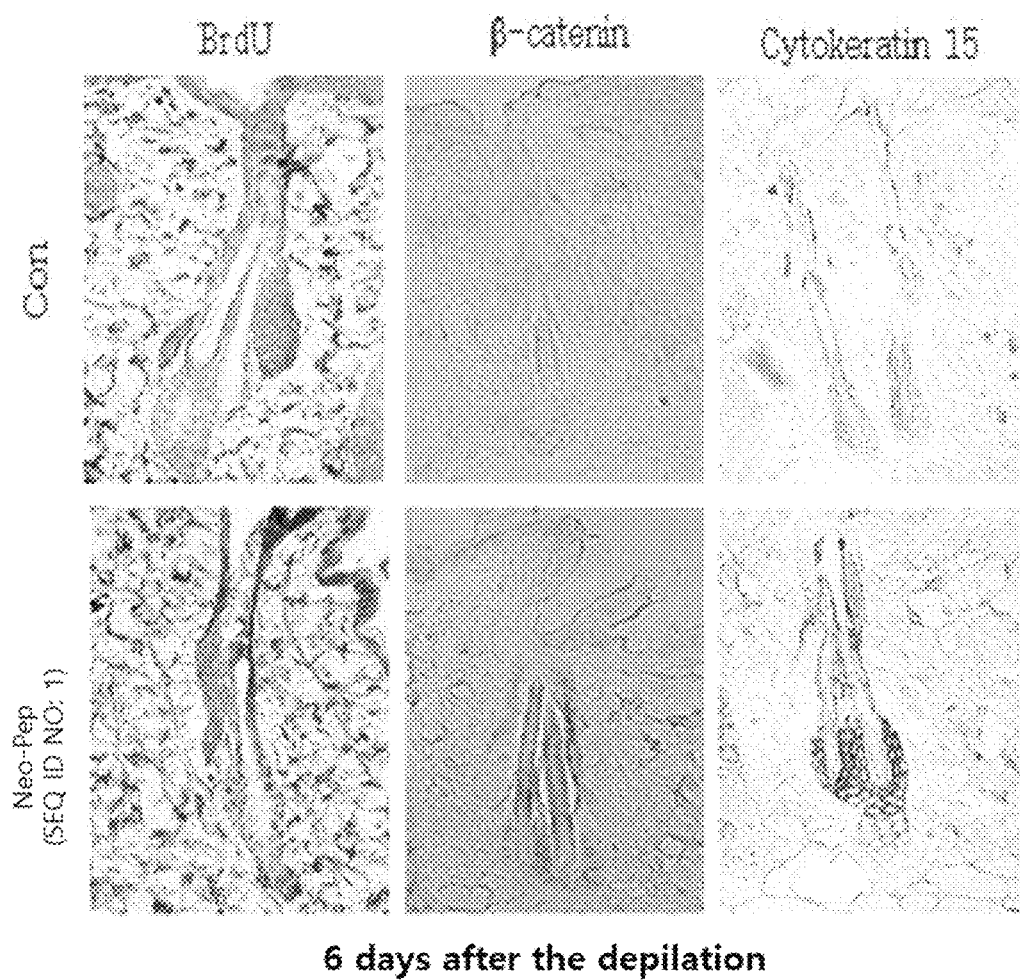
FIG. 3 shows the cross-sectional images of the skin tissue and hair follicle region observed through a phase contrast microscope in order to compare the hair growth in the control group and the Neo-Pep polypeptide (polypeptide of SEQ ID NO: 1) treated group at Day 6 after depilation. As can be seen from the results of the proliferation of BrdU (cell proliferation marker), β-catenin (signaling marker of hair follicle cell) and Cytokeratin 15 (hair follicle stem cell marker), it was confirmed that the anagen phase starts earlier in Neo-Pep polypeptide (polypeptide of SEQ ID NO: 1) treated group than the control group [Control (Con): 20% Glycerol/PBS; Neo-Pep polypeptide (polypeptide of SEQ ID NO: 1, 100 nM)].

Example 2: Effect of the Polypeptide of the Present Invention on Inducing Proliferation of Hair Follicle Stem Cell Through β-Catenin Signaling β-catenin is a very important protein for hair growth and a very important factor in follicular stem cell proliferation playing a role as a signaling marker for hair follicle cells. In addition, Cytokeratin 15 acts as a biomarker of hair follicle stem cells, and BrdU is known to be a factor that plays a role as a cell growth marker. FIG. 3 shows the cross-sectional images of the skin tissue and hair follicle region observed through a phase contrast microscope in order to compare the hair growth in the control group and the Neo-Pep polypeptide (polypeptide of SEQ ID NO: 1) treated group at Day 6 after depilation. As can be seen from the results of the BrdU (cell proliferation marker), β-catenin (signaling marker of hair follicle cell) and Cytokeratin 15 (hair follicle stem cell marker), it was confirmed that the anagen phase starts earlier in Neo-Pep polypeptide (polypeptide of SEQ ID NO: 1) treated group than the control group.

Figure 4:
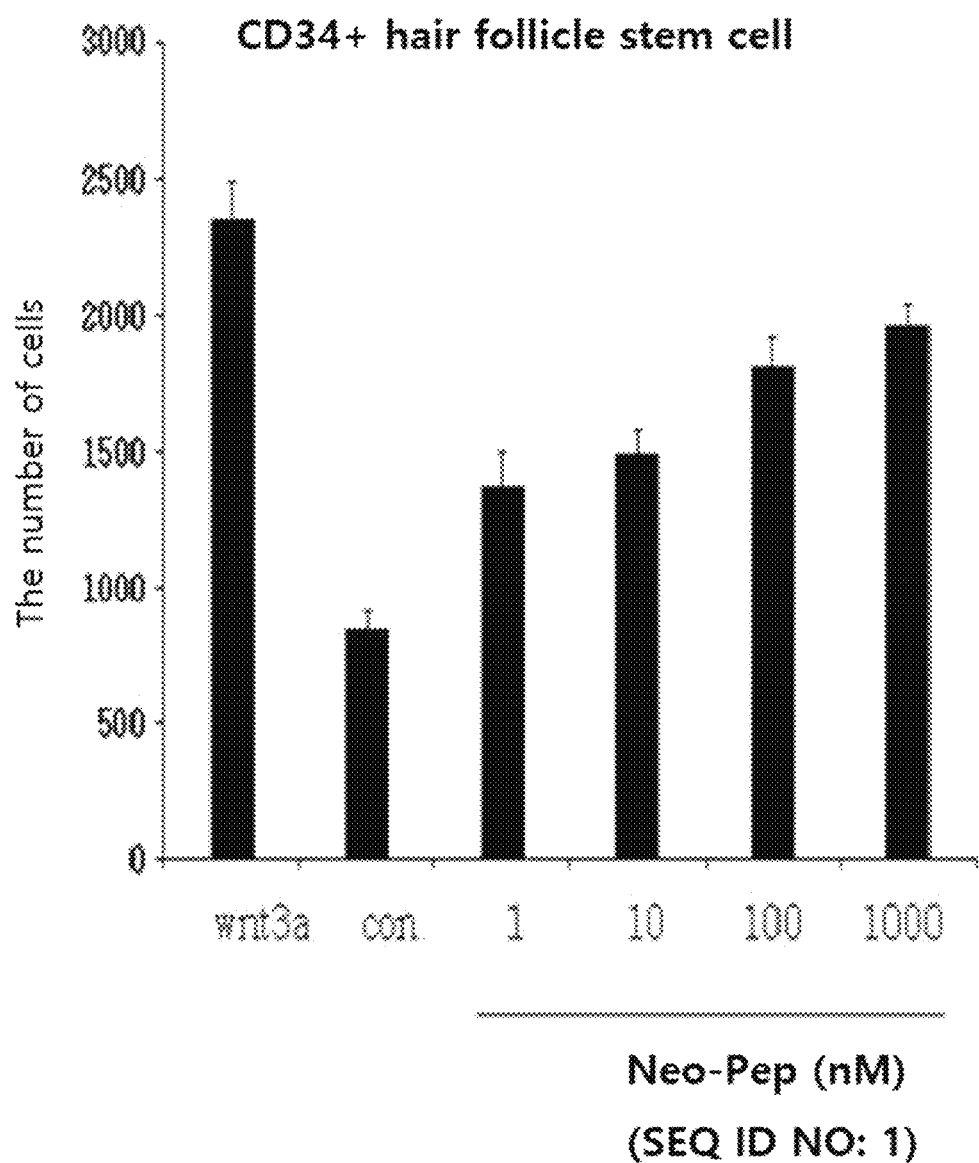
FIG. 4 shows in vitro assay results showing that the Neo-Pep polypeptide (polypeptide of SEQ ID NO: 1) induces the proliferation of CD34+ hair follicle stem cells in a concentration dependent manner (1 nM, 10 nM, 100 nM, 1000 nM).
Figure 5:
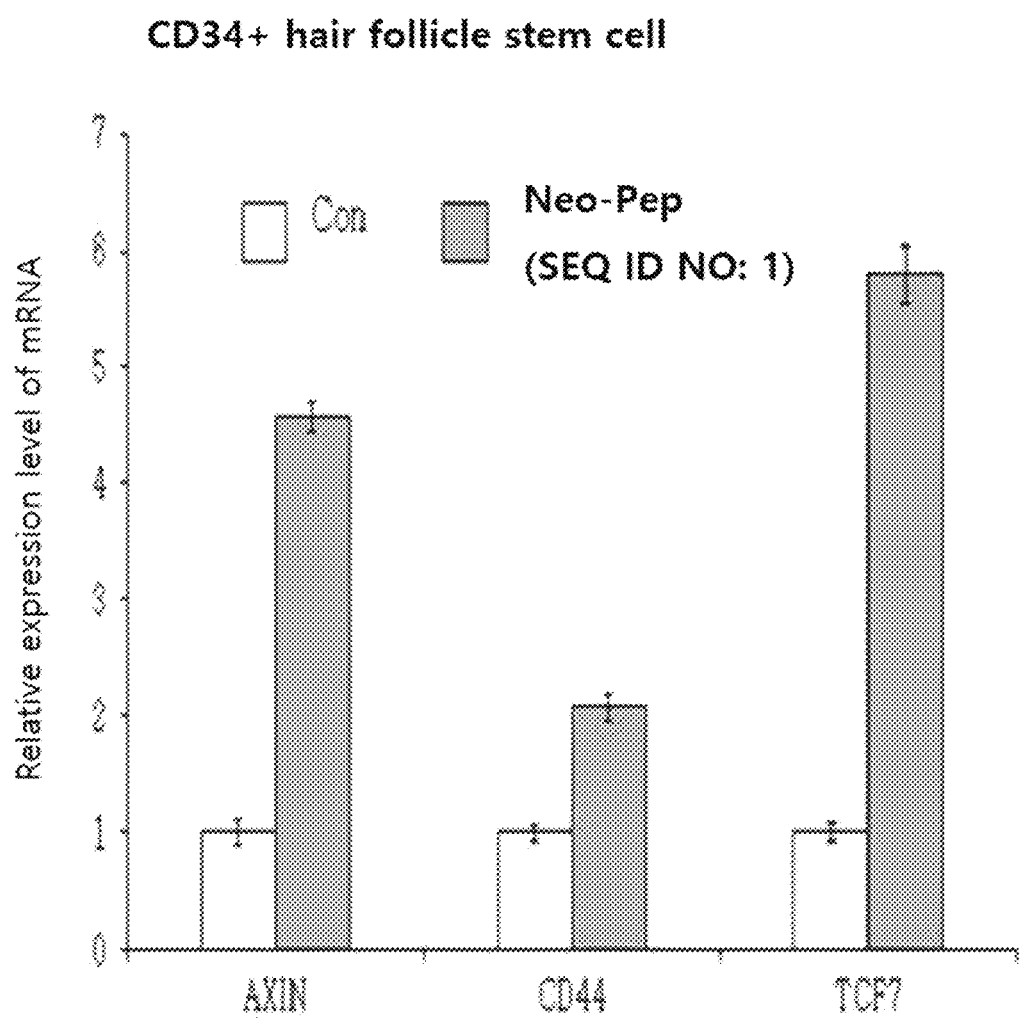
FIG. 5 is a graph showing in vitro assay results that the Neo-Pep polypeptide (polypeptide of SEQ ID NO: 1, 100 nM) induces the proliferation of CD34+ hair follicle stem cells through the β-catenin pathway, and it was confirmed that the mRNA expression of AXIN, CD44 and TCF which are target gene of β-catenin was increased by treatment of polypeptide of the present invention[Control (Con): 20% Glycerol/PBS; Neo-Pep polypeptide (polypeptide of SEQ ID NO: 1, 100 nM)].

In addition, as can be seen from the graph of in vitro assay of hair growth in FIG. 4, the Neo-Pep polypeptide (polypeptide of SEQ ID NO: 1) induced proliferation of CD34+ hair follicle stem cells in a dose-dependent manner (1 nM, 10 nM, 100 nM and 1000 nM). As shown in the in vitro assay result graph of FIG. 5, it was confirmed that the Neo-Pep polypeptide (polypeptide of SEQ ID NO: 1, 100 nM) induces the proliferation of CD34+ hair follicle stem cells through the β-catenin pathway. Specifically, when the Neo-Pep polypeptide (polypeptide of SEQ ID NO: 1, 100 nM) according to the present invention is used, the mRNA expression level of AXIN, CD44 and TCF7, which are the target genes of β-catenin, increased 5-fold compared to the control group.

Example 3: Effect on Promoting Hair Growth in Alopecia Areata Mouse Model

Alopecia areata is known to be a cell-mediated autoimmune disease that targets hair follicles of anagen phase in various mammalian species. In humans, alopecia areata is divided into three classes: alopecia areata (patchy hair loss), alopecia totalis (hair loss on the head), and alopecia universalis (total body hair loss).

In order to confirm the effect of the polypeptide of the present invention on the human hair growth cycle, C3H/HeJ mouse (Jackson Laboratory, USA) was used as an animal model reflecting the pathological state of human alopecia areata. The advantage of using the C3H/HeJ mouse is that when full thickness skin graft is applied to an aged mouse having alopecia areata from young age, patchy alopecia develops within 8 to 10 weeks, and after 20 weeks, alopecia extends to the whole body skin and result in a chronic state of alopecia universalis.

In this test, C3H/HeJ female mice having alopecia universalis that was induced 25 weeks after skin transplantation as described above were used. Without any pretreatment such as shaving or depilation, control group (Control-treated mice, 100 µl of 20% glycerol/PBS) and Neo-Pep polypeptide treated group (Peptide-treated mice, 100 µl of 100 nM Neo-Pep polypeptide (SEQ ID NO: 1) in 20% glycerol/PBS) were treated with each test material topically around the alopecia region using brush, once daily, for 14 weeks. Control group and Neo-Pep treated group consisted of 4 mice, respectively.

Figure 6:
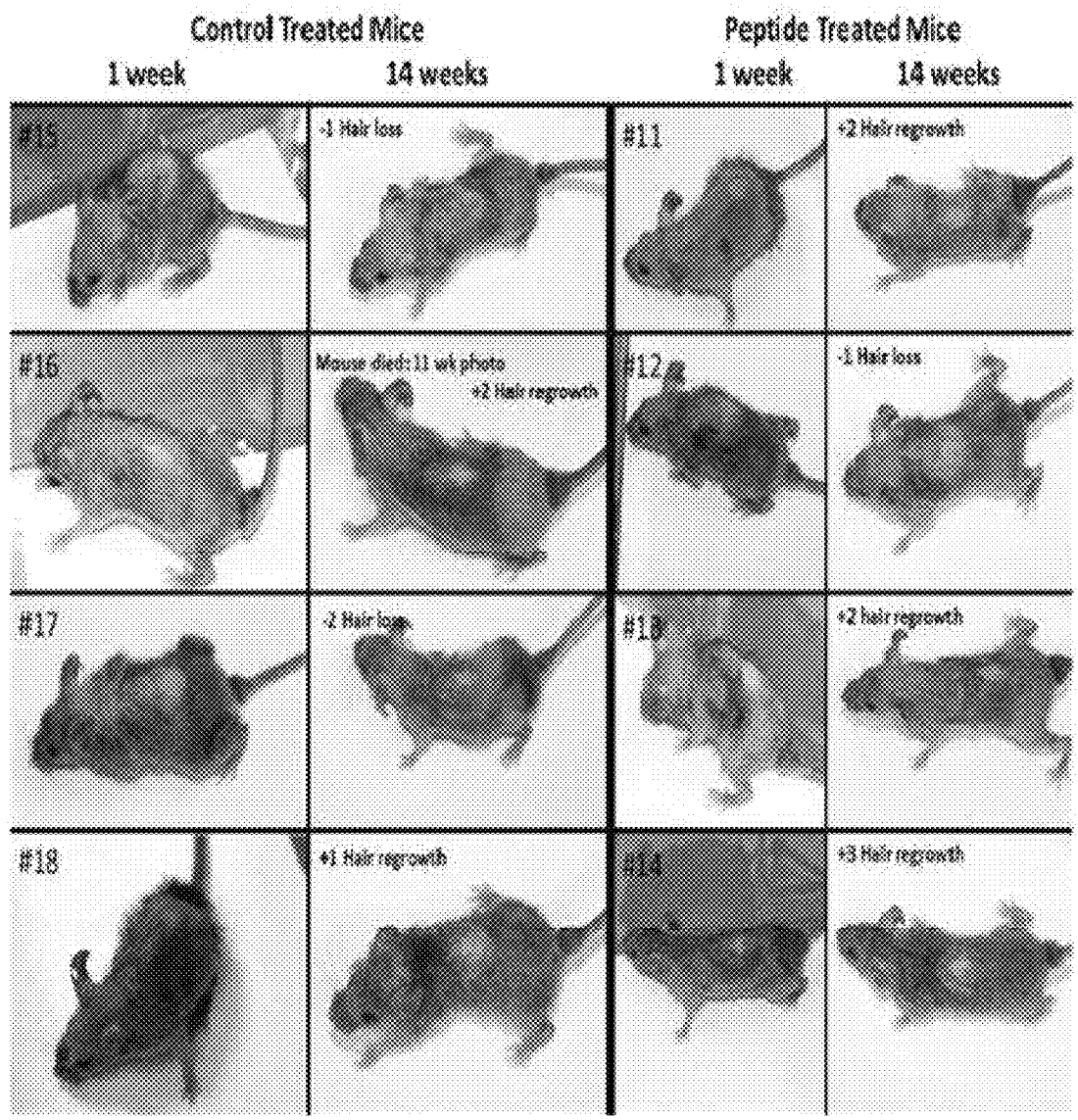
FIG. 6 is images showing the effect of promoting hair growth using C3H/HeJ mice having a skin graft cell-induced alopecia areata [(Control treated mice: 100 µl of 20% glycerol/PBS); Neo-Pep polypeptide-treated group (Peptide-treated mice, 100 µl of 100 nM Neo-Pep polypeptide (SEQ ID NO: 1) in 20% glycerol/PBS).

Photographs were taken every 2 weeks from the beginning of the experiment. FIG. 6 shows the state of hair growth of mice at 1 week and 14 weeks after the beginning of the experiment. In the case of Neo-Pep polypeptide-treated group (peptide-treated mice, 100 nM Neo-Pep polypeptide (SEQ ID NO: 1) in 20% glycerol/PBS), hair began to grow again after 11 weeks of administration, and mild to moderate hair growth was observed in 3 out of 4 mice (#11, #13, and #14 mice) showing consistent hair growth effect. In contrast, the control group showed mild hair growth effect in only 1 mouse (#18 mouse) out of 4 mice, alopecia of 2 mice (#15 and #17 mouse) became more severe, and 1 (#16 mouse) died before the end of the experiment, thus showing no consistent hair growth effect.

Figure 7:
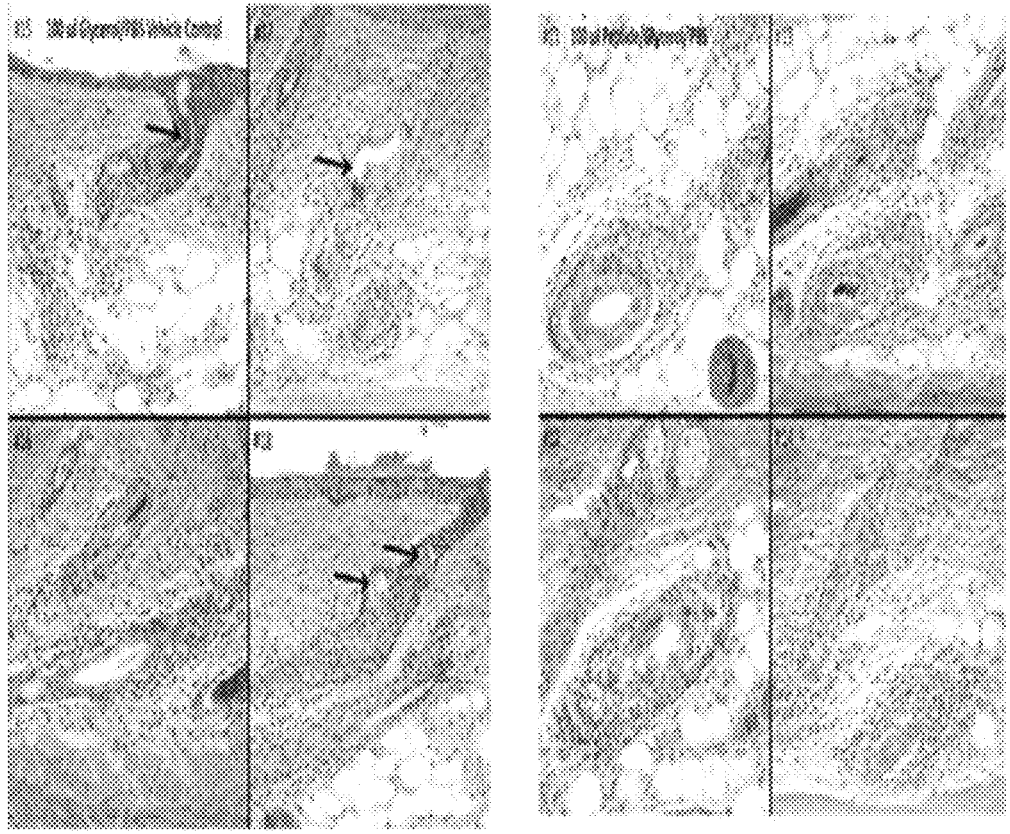
FIG. 7 is images showing the state of hair follicles and presence or absence of inflammation in the skin tissue sections of C3H/HeJ mice having a skin graft cell-induced alopecia areata [(Control treated mice: 100 µl of 20% glycerol/PBS); Neo-Pep polypeptide-treated group (Peptide-treated mice, 100 µl of 100 nM Neo-Pep polypeptide (SEQ ID NO: 1) in 20% glycerol/PBS).

Meanwhile, in the images of the skin tissue of the mouse in FIG. 7, the skin tissue at the alopecia area and the area without alopecia around it was collected, fixed in Fekete's acid alcohol formalin and analyzed for H&E staining. And FIG. 7 shows results confirming the presence or absence of deformation or inflammation, and the state of hair follicle.

As can be seen from FIG. 7, especially in the skin tissue of the control group, complex infiltration of inflammatory cells in the hair follicles and around the hair follicles was observed, and especially lymphocyte infiltration was frequently found. These are main characteristics used for diagnosing alopecia areata. And follicular dystrophy is a phenomenon that occurs frequently in alopecia areata, which means that hair follicles are twisted and deformed or have weak or disrupted hair shaft.

As can be seen from FIG. 7, inflammation and deformed hair shaft were developed in the skin of the control group. On the other hand, the development of inflammation and deformed hair shaft was significantly lower in Neo-Pep polypeptide treated group compared to the control group. The overall alopecia state changes depending on the hair shaft breakage near the skin surface or skin surface. And the alopecia state was more clearly observed in the control group where the malformed hair shaft such as hair shaft breakage was relatively more.

Example 4: Effect of the Polypeptide of the Present Invention on Proliferation of Hair Follicle Stem Cells The present inventor prepared N1 (SEQ ID NO: 2), N2 (SEQ ID NO: 3), N3 (SEQ ID NO: 4), N4 (SEQ ID NO: 5), N5 (SEQ ID NO: 6), N6 (SEQ ID NO: 7), N7 (SEQ ID NO: 8) and N8 (SEQ ID NO: 9) in order to identify peptide fragments having the effect on promoting hair growth and improving alopecia in the Neo-Pep polypeptide (SEQ ID NO: 1) in which the hair growth promoting effect was confirmed in the above Examples.

Table 1 below shows the amino acid sequence, PI and Tm of Neo-Pep (SEQ ID NO: 1) and its fragments, N1 (SEQ ID NO: 2), N2 (SEQ ID NO: 3), N3 (SEQ ID NO: 4), N4 (SEQ ID NO: 5), N5 (SEQ ID NO: 6), N6 (SEQ ID NO: 7), N7 (SEQ ID NO: 8) and N8 (SEQ ID NO: 9).

TABLE 1

| Polypeptide (SEQ ID) | Amino acid sequence | | PI | Tm |
| --- | --- | --- | --- | --- |
| Neo-Pep (SEQ ID NO: 1) | AVLKRLEQKGAEADQIIEYLKQQVSLLKEKAILQATLREEK | 6 46 | 9.33 | >65 |
| N1 (SEQ ID NO: 2) | AVLKRLEQKGAEADQIIEYL | | 4.64 | 55~65 |
| N2 (SEQ ID NO: 3) | LKRLEQKGAEADQIIEYLKQ | | 7.05 | <55 |
| N3 (SEQ ID NO: 4) | KGAEADQIIEYLKQQVSLLK | | 7.01 | 55~65 |

TABLE 1-continued

| Polypeptide (SEQ ID) | Amino acid sequence | PI | Tm |
|---|---|---|---|
| N4 (SEQ ID NO: 5) | AEADQIIEYLKQQVSLLKEK | 4.64 | 55~65 |
| N5 (SEQ ID NO: 6) | IEYLKQQVSLLKEKAILQAT | 9.53 | >65 |
| N6 (SEQ ID NO: 7) | YLKQQVSLLKEKAILQATLR | 10.56 | >65 |
| N7 (SEQ ID NO: 8) | KQQVSLLKEKAILQATLREE | 9.8 | >65 |
| N8 (SEQ ID NO: 9) | QVSLLKEKAILQATLREEK | 9.8 | 55~65 |

For reference, the polypeptide Neo-Pep (SEQ ID NO: 1) of the present invention corresponds to the 6$^{th}$ to 46$^{th}$ amino acid residue in the AIMP1 protein (SEQ ID NO: 16).

MANNDAVLKRLEQKGAEADQIIEYLKQQVSLLKEKAILQATLREEKKLRV

ENAKLKKEIEELKQELIQAEIQNGVKQIPFPSGTPLHANSMVSENVIQST

AVTTVSSGTKEQIKGGTGDEKKAKEKIEKKGEKKEKKQQSIAGSADSKPI

DVSRLDLRIGCIITARKHPDADSLYVEEVDVGEIAPRTVVSGLVNHVPLE

QMQNRMVILLCNLKPAKMRGVLSQAMVMCASSPEKIEILAPPNGSVPGDR

ITFDAFPGEPDKELNPKKKIWEQIQPDLHTNDECVATYKGVPFEVKGKGV

CRAQTMSNSGIK

Figure 8:
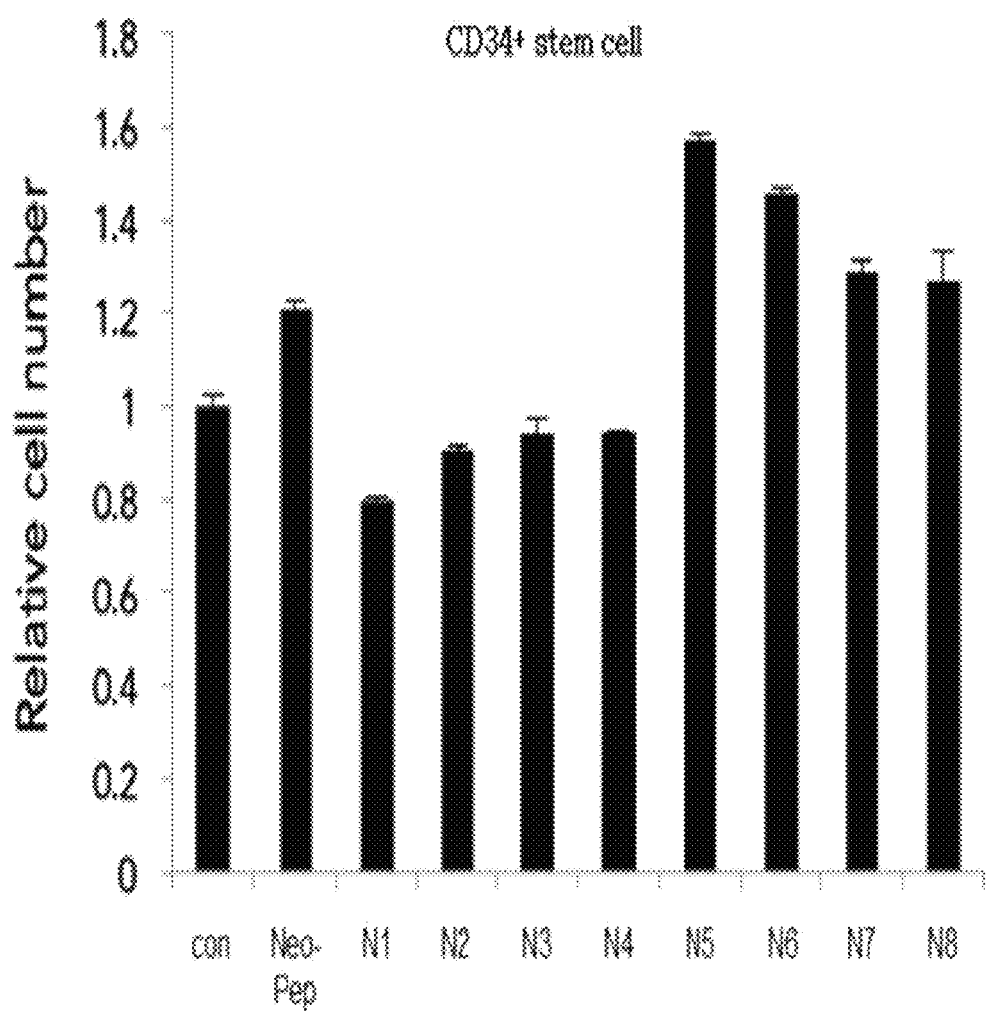
FIG. 8 is a graph showing in vitro assay results confirming the effect on promoting the proliferation of CD34+ hair follicle stem cells with the Neo-Pep polypeptide of the present invention (SEQ ID NO: 1) and its fragment having 19 or 20 amino acids (N1: SEQ ID NO: 2, N2: SEQ ID NO: 3, N3: SEQ ID NO: 4, N4: SEQ ID NO: 5, N5: SEQ ID NO: 6, N6: SEQ ID NO: 7, N7: SEQ ID NO: 8 and N8: SEQ ID NO: 9)(each peptide was treated at the concentration of 100 nM).

CD34+ hair follicle stem cells in vitro assay and BrdU proliferation assay method described above were used. As can be seen in FIG. 8 in which the relative number of CD34+ hair follicle stem cell was compared, Neo-Pep (SEQ ID NO: 1), and its fragments (N5 (SEQ ID NO: 6), N6 (SEQ ID NO: 7), N7 (SEQ ID NO: 8) and N8 (SEQ ID NO: 9)) comprising 28$^{th}$ to 31$^{st}$ amino acid residue (KEKA) of Neo-Pep polypeptide and consisting of or 20 consecutive amino acids induced proliferation of CD34+ hair follicle stem cells.

On the other hand, fragments (N1 (SEQ ID NO: 2), N2 (SEQ ID NO: 3), N3 (SEQ ID NO: 4) and N4 (SEQ ID NO: 5)) of Neo-Pep (SEQ ID NO: 1) consisting of 20 consecutive amino acids without 28$^{th}$ to 31$^{st}$ amino acid residue (KEKA) of Neo-Pep polypeptide didn't show any effect on inducing proliferation of CD34+ hair follicle stem cells.

Through the above results, it was confirmed that not only Neo-Pep polypeptide (SEQ ID NO: 1) but also polypeptide fragments which comprise 28$^{th}$ to 31$^{st}$ amino acid residue of Neo-Pep polypeptide as an active amino acid residue and consist of consecutive amino acids have effect on promoting hair growth and improving alopecia.

Example 5: Effect of the Polypeptide of the Present Invention on Promoting In Vivo Hair Growth The present inventor prepared N9 (SEQ ID NO: 10), N10 (SEQ ID NO: 11), N11 (SEQ ID NO: 12), N12 (SEQ ID NO: 13), N13 (SEQ ID NO: 14) and N14 (SEQ ID NO: 15), which are polypeptide fragments consisting of 15 amino acids, in order to further identify peptide fragments having the effect on promoting hair growth and improving alopecia in the Neo-Pep polypeptide (SEQ ID NO: 1) in which the hair growth promoting effect was confirmed in the above Examples.

Table 2 below shows the amino acid sequence, PI and Tm of Neo-Pep (SEQ ID NO: 1) and its fragments, N9 (SEQ ID NO: 10), N10 (SEQ ID NO: 11), N11 (SEQ ID NO: 12), N12 (SEQ ID NO: 13), N13 (SEQ ID NO: 14) and N14 (SEQ ID NO: 15).

TABLE 2

| Polypeptide (SEQ ID) | Amino acid sequence | PI | Tm |
|---|---|---|---|
| Neo-Pep (SEQ ID NO: 1) | 6                                                46<br>AVLKRLEQKGAEADQIIEYLKQQVSLLKEKAILQATLREEK | 9.33 | >65 |
| N9 (SEQ ID NO: 10) | AVLKRLEQKGAEADQ | 7.08 | >65 |
| N10 (SEQ ID NO: 11) | EADQIIEYLKQQVSL | 3.66 | >65 |
| N11 (SEQ ID NO: 12) | ADQIIEYLKQQVSLL | 3.99 | >65 |

TABLE 2-continued

| Polypeptide (SEQ ID) | Amino acid sequence | PI | Tm |
|---|---|---|---|
| N12 (SEQ ID NO: 13) | IEYLKQQVSLLKEKA | 9.53 | >65 |
| N13 (SEQ ID NO: 14) | KQQVSLLKEKAILQA | 10.41 | >65 |
| N14 (SEQ ID NO: 15) | LKEKAILQATLREEK | 9.8 | <55 |

Figure 9:
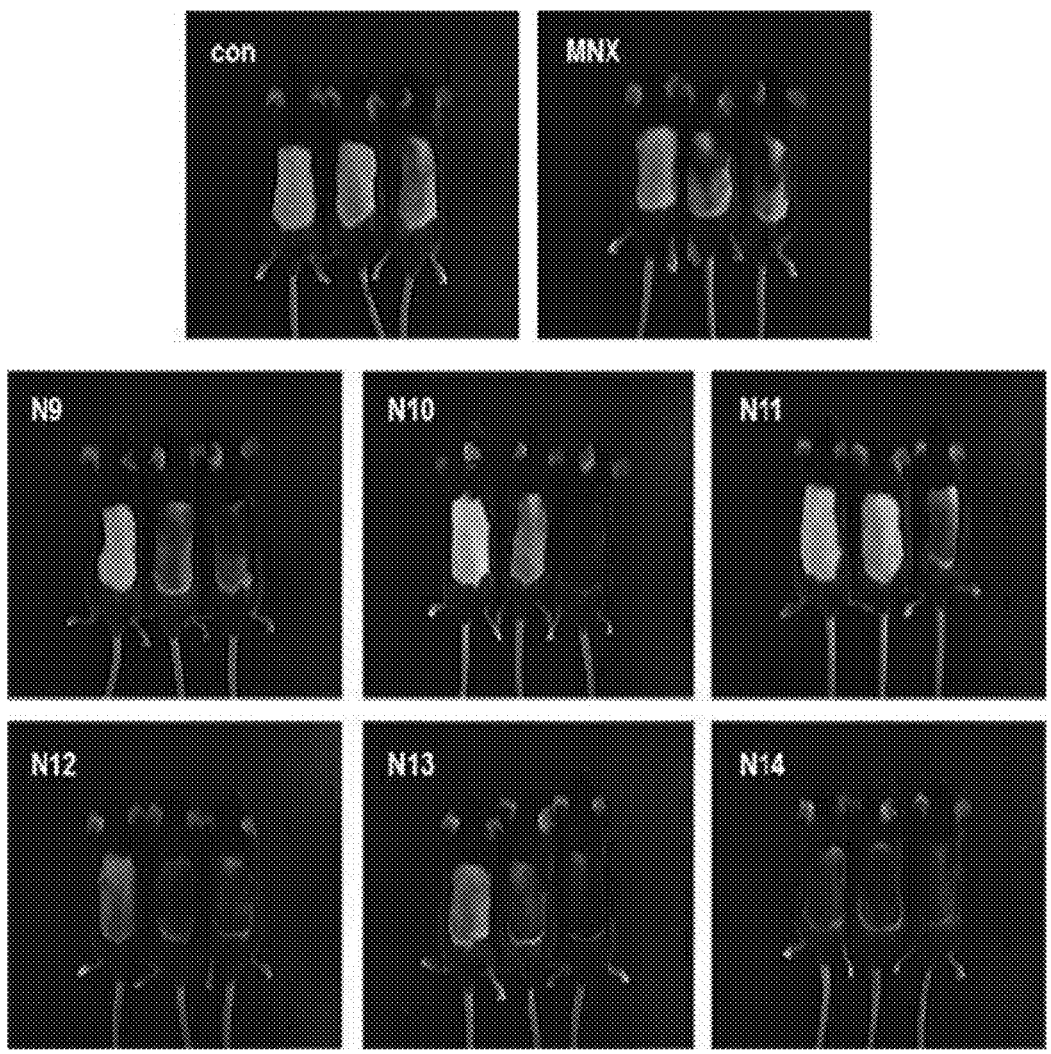
FIG. 9 is images confirming the in vivo hair growth promoting effect of fragments of Neo-Pep polypeptide of the present invention (SEQ ID NO: 1), wherein the fragments consist of 15 amino acids (N9: SEQ ID NO: 10, N10: SEQ ID NO: 11, N11: SEQ ID NO: 12, N12: SEQ ID NO: 13, N13: SEQ ID NO: 14 and N14: SEQ ID NO: 15) [Control (con): 20% Glyceol/PBS; 3% Minoxidil (MNX, 140 mM); N9 to N14 polypeptide fragments (SEQ ID NO: 10 to 15, 100 nM)]

As can be seen in FIG. 9 (dorsal skin images of mice at 13 days after depilation using the same method as in Example 1), dorsal hair of the mouse group treated with the polypeptide fragments of the present invention (N12 (SEQ ID NO: 13), N13 (SEQ ID NO: 14) and N14 (SEQ ID NO: 15)) comprising $28^{th}$ to $31^{st}$ amino acid residue (KEKA) of Neo-Pep polypeptide and consisting of 15 consecutive amino acids grew much more than control group (Con, 20% glycerol/PBS treated group), and grew even similar to or much more than positive control group (MNX, 3% Minoxidil treated group).

On the other hand, fragments (N9 (SEQ ID NO: 10), N10 (SEQ ID NO: 11) and N11 (SEQ ID NO: 12)) of Neo-Pep (SEQ ID NO: 1) consisting of 15 consecutive amino acids without $28^{th}$ to $31^{st}$ amino acid residue (KEKA) of Neo-Pep polypeptide didn't show such effect.

Through the above results, it was further confirmed that polypeptide fragments such as N12 (SEQ ID NO: 13), N13 (SEQ ID NO: 14) and N14 (SEQ ID NO: 15), which comprise $28^{th}$ to $31^{st}$ amino acid residue of Neo-Pep polypeptide (SEQ ID NO: 1) as an active amino acid residue and consist of consecutive amino acids, have effect on promoting hair growth and improving alopecia. Thus, it was confirmed that comprising the $28^{th}$ to $31^{st}$ amino acid residue (KEKA) of the Neo-Pep polypeptide (SEQ ID NO: 1) as an active site is essential for effect on promoting hair growth and improving alopecia.

The invention claimed is:

1. A method for promoting hair growth, promoting proliferation of hair follicle stem cells, or preventing and treating alopecia, the method comprising administering to a subject in need thereof an effective amount of a composition comprising one or more polypeptides as an active ingredient selected from the group consisting of a polypeptide consisting of 15 to 20 consecutive amino acids from the amino acid sequence of SEQ ID NO: 1, wherein the polypeptide comprises the 28$^{th}$ to 31$^{st}$ amino acid residue (KEKA) of the amino acid sequence of SEQ ID NO: 1 and promotes hair growth, promotes proliferation of hair follicle stem cells, and/or treats alopecia, and wherein the polypeptide consists of one of the amino acid sequences selected from the group consisting of SEQ ID NO: 6, SEQ ID NO: 7, SEQ ID NO: 8, SEQ ID NO: 9, SEQ ID NO: 13, SEQ ID NO: 14 and SEQ ID NO: 15.

2. The method of claim 1, wherein the composition further comprises a compound or pharmaceutically acceptable salt thereof selected from the group consisting of minoxidil, cromakalim, pinacidil, naminidil, diphenylcyclopropenone, cyproterone acetate, danazol, flutamide; 5-alpha reductase inhibitors selected from the group consisting of finasteride, turosteride, LY-191704, MK-306 and dutasteride; s-triazines, benzopyrans, pyridinopyrans and thiane-1-oxides.

* * * * *

SEQUENCE LISTING

```
<160> NUMBER OF SEQ ID NOS: 41

<210> SEQ ID NO 1
<211> LENGTH: 41
<212> TYPE: PRT
<213> ORGANISM: Artificial Sequence
<220> FEATURE:
<223> OTHER INFORMATION: Homo sapiens Neo-Pep polypeptide; AIMP1-(6-46)

<400> SEQUENCE: 1

Ala Val Leu Lys Arg Leu Glu Gln Lys Gly Ala Glu Ala Asp Gln Ile
1               5                   10                  15

Ile Glu Tyr Leu Lys Gln Gln Val Ser Leu Leu Lys Glu Lys Ala Ile
            20                  25                  30

Leu Gln Ala Thr Leu Arg Glu Glu Lys
        35                  40

<210> SEQ ID NO 2
<211> LENGTH: 20
<212> TYPE: PRT
<213> ORGANISM: Artificial Sequence
<220> FEATURE:
<223> OTHER INFORMATION: Homo sapiens N1 polypeptide; Neo-Pep-(1-20)

<400> SEQUENCE: 2

Ala Val Leu Lys Arg Leu Glu Gln Lys Gly Ala Glu Ala Asp Gln Ile
1               5                   10                  15

Ile Glu Tyr Leu
            20

<210> SEQ ID NO 3
<211> LENGTH: 20
<212> TYPE: PRT
```

-continued

```
<213> ORGANISM: Artificial Sequence
<220> FEATURE:
<223> OTHER INFORMATION: Homo sapiens N2 polypeptide; Neo-Pep-(3-22)

<400> SEQUENCE: 3

Leu Lys Arg Leu Glu Gln Lys Gly Ala Glu Ala Asp Gln Ile Ile Glu
1               5                   10                  15

Tyr Leu Lys Gln
            20

<210> SEQ ID NO 4
<211> LENGTH: 20
<212> TYPE: PRT
<213> ORGANISM: Artificial Sequence
<220> FEATURE:
<223> OTHER INFORMATION: Homo sapiens N3 polypeptide; Neo-Pep-(9-28)

<400> SEQUENCE: 4

Lys Gly Ala Glu Ala Asp Gln Ile Ile Glu Tyr Leu Lys Gln Gln Val
1               5                   10                  15

Ser Leu Leu Lys
            20

<210> SEQ ID NO 5
<211> LENGTH: 20
<212> TYPE: PRT
<213> ORGANISM: Artificial Sequence
<220> FEATURE:
<223> OTHER INFORMATION: Homo sapiens N4 polypeptide; Neo-Pep-(11-30)

<400> SEQUENCE: 5

Ala Glu Ala Asp Gln Ile Ile Glu Tyr Leu Lys Gln Gln Val Ser Leu
1               5                   10                  15

Leu Lys Glu Lys
            20

<210> SEQ ID NO 6
<211> LENGTH: 20
<212> TYPE: PRT
<213> ORGANISM: Artificial Sequence
<220> FEATURE:
<223> OTHER INFORMATION: Homo sapiens N5 polypeptide; Neo-Pep-(17-36)

<400> SEQUENCE: 6

Ile Glu Tyr Leu Lys Gln Gln Val Ser Leu Leu Lys Glu Lys Ala Ile
1               5                   10                  15

Leu Gln Ala Thr
            20

<210> SEQ ID NO 7
<211> LENGTH: 20
<212> TYPE: PRT
<213> ORGANISM: Artificial Sequence
<220> FEATURE:
<223> OTHER INFORMATION: Homo sapiens N6 polypeptide; Neo-Pep-(19-38)

<400> SEQUENCE: 7

Tyr Leu Lys Gln Gln Val Ser Leu Leu Lys Glu Lys Ala Ile Leu Gln
1               5                   10                  15

Ala Thr Leu Arg
            20

<210> SEQ ID NO 8
<211> LENGTH: 20
```

```
<212> TYPE: PRT
<213> ORGANISM: Artificial Sequence
<220> FEATURE:
<223> OTHER INFORMATION: Homo sapiens N7 polypeptide; Neo-Pep-(21-40)

<400> SEQUENCE: 8

Lys Gln Gln Val Ser Leu Leu Lys Glu Lys Ala Ile Leu Gln Ala Thr
1               5                   10                  15

Leu Arg Glu Glu
            20

<210> SEQ ID NO 9
<211> LENGTH: 19
<212> TYPE: PRT
<213> ORGANISM: Artificial Sequence
<220> FEATURE:
<223> OTHER INFORMATION: Homo sapiens N8 polypeptide; Neo-Pep-(23-41)

<400> SEQUENCE: 9

Gln Val Ser Leu Leu Lys Glu Lys Ala Ile Leu Gln Ala Thr Leu Arg
1               5                   10                  15

Glu Glu Lys

<210> SEQ ID NO 10
<211> LENGTH: 15
<212> TYPE: PRT
<213> ORGANISM: Artificial Sequence
<220> FEATURE:
<223> OTHER INFORMATION: Homo sapiens N9 polypeptide; Neo-Pep-(1-15)

<400> SEQUENCE: 10

Ala Val Leu Lys Arg Leu Glu Gln Lys Gly Ala Glu Ala Asp Gln
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Homo sapiens N10 polypeptide; Neo-Pep-(12-26)

<400> SEQUENCE: 11

Glu Ala Asp Gln Ile Ile Glu Tyr Leu Lys Gln Gln Val Ser Leu
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Homo sapiens N11 polypeptide; Neo-Pep-(13-27)

<400> SEQUENCE: 12

Ala Asp Gln Ile Ile Glu Tyr Leu Lys Gln Gln Val Ser Leu Leu
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Homo sapiens N12 polypeptide; Neo-Pep-(17-31)

<400> SEQUENCE: 13

Ile Glu Tyr Leu Lys Gln Gln Val Ser Leu Leu Lys Glu Lys Ala
1               5                   10                  15
```

<210> SEQ ID NO 14
<211> LENGTH: 15
<212> TYPE: PRT
<213> ORGANISM: Artificial Sequence
<220> FEATURE:
<223> OTHER INFORMATION: Homo sapiens N13 polypeptide; Neo-Pep-(21-35)

<400> SEQUENCE: 14

Lys Gln Gln Val Ser Leu Leu Lys Glu Lys Ala Ile Leu Gln Ala
 1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Homo sapiens N14 polypeptide; Neo-Pep-(27-41)

<400> SEQUENCE: 15

Leu Lys Glu Lys Ala Ile Leu Gln Ala Thr Leu Arg Glu Glu Lys
 1               5                  10                  15

<210> SEQ ID NO 16
<211> LENGTH: 312
<212> TYPE: PRT
<213> ORGANISM: Artificial Sequence
<220> FEATURE:
<223> OTHER INFORMATION: homo sapiens AIMP1 protein

<400> SEQUENCE: 16

Met Ala Asn Asn Asp Ala Val Leu Lys Arg Leu Glu Gln Lys Gly Ala
 1               5                  10                  15

Glu Ala Asp Gln Ile Ile Glu Tyr Leu Lys Gln Gln Val Ser Leu Leu
                20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Pro Phe
65                  70                  75                  80

Pro Ser Gly Thr Pro Leu His Ala Asn Ser Met Val Ser Glu Asn Val
                85                  90                  95

Ile Gln Ser Thr Ala Val Thr Thr Val Ser Ser Gly Thr Lys Glu Gln
            100                 105                 110

Ile Lys Gly Gly Thr Gly Asp Glu Lys Lys Ala Lys Glu Lys Ile Glu
        115                 120                 125

Lys Lys Gly Glu Lys Lys Glu Lys Lys Gln Gln Ser Ile Ala Gly Ser
    130                 135                 140

Ala Asp Ser Lys Pro Ile Asp Val Ser Arg Leu Asp Leu Arg Ile Gly
145                 150                 155                 160

Cys Ile Ile Thr Ala Arg Lys His Pro Asp Ala Asp Ser Leu Tyr Val
                165                 170                 175

Glu Glu Val Asp Val Gly Glu Ile Ala Pro Arg Thr Val Val Ser Gly
            180                 185                 190

Leu Val Asn His Val Pro Leu Glu Gln Met Gln Asn Arg Met Val Ile
        195                 200                 205

Leu Leu Cys Asn Leu Lys Pro Ala Lys Met Arg Gly Val Leu Ser Gln
    210                 215                 220

```
Ala Met Val Met Cys Ala Ser Ser Pro Glu Lys Ile Glu Ile Leu Ala
225                 230                 235                 240

Pro Pro Asn Gly Ser Val Pro Gly Asp Arg Ile Thr Phe Asp Ala Phe
            245                 250                 255

Pro Gly Glu Pro Asp Lys Glu Leu Asn Pro Lys Lys Ile Trp Glu
        260                 265                 270

Gln Ile Gln Pro Asp Leu His Thr Asn Asp Glu Cys Val Ala Thr Tyr
        275                 280                 285

Lys Gly Val Pro Phe Glu Val Lys Gly Lys Gly Val Cys Arg Ala Gln
    290                 295                 300

Thr Met Ser Asn Ser Gly Ile Lys
305                 310

<210> SEQ ID NO 17
<211> LENGTH: 123
<212> TYPE: DNA
<213> ORGANISM: Artificial Sequence
<220> FEATURE:
<223> OTHER INFORMATION: Homo sapiens Neo-Pep AIMP1-(6-46) polynuceotide

<400> SEQUENCE: 17
gctgttctga agagactgga gcagaagggt gcagaggcag atcaaatcat tgaatatctt    60
aagcagcaag tttctctact taaggagaaa gcaattttgc aggcaacttt gagggaagag   120
aag                                                                 123

<210> SEQ ID NO 18
<211> LENGTH: 60
<212> TYPE: DNA
<213> ORGANISM: Artificial Sequence
<220> FEATURE:
<223> OTHER INFORMATION: Homo sapiens N1 Neo-Pep-(1-20) polynucleotide

<400> SEQUENCE: 18
gctgttctga agagactgga gcagaagggt gcagaggcag atcaaatcat tgaatatctt    60

<210> SEQ ID NO 19
<211> LENGTH: 60
<212> TYPE: DNA
<213> ORGANISM: Artificial Sequence
<220> FEATURE:
<223> OTHER INFORMATION: Homo sapiens N2 Neo-Pep-(3-22) polynucleotide

<400> SEQUENCE: 19
ctgaagagac tggagcagaa gggtgcagag gcagatcaaa tcattgaata tcttaagcag    60

<210> SEQ ID NO 20
<211> LENGTH: 60
<212> TYPE: DNA
<213> ORGANISM: Artificial Sequence
<220> FEATURE:
<223> OTHER INFORMATION: Homo sapiens N3 Neo-Pep-(9-28) polynucleotide

<400> SEQUENCE: 20
aagggtgcag aggcagatca aatcattgaa tatcttaagc agcaagtttc tctacttaag    60

<210> SEQ ID NO 21
<211> LENGTH: 60
<212> TYPE: DNA
<213> ORGANISM: Artificial Sequence
<220> FEATURE:
<223> OTHER INFORMATION: Homo sapiens N4 Neo-Pep-(11-30) polynucleotide

<400> SEQUENCE: 21
```
gcagaggcag atcaaatcat tgaatatctt aagcagcaag tttctctact taaggagaaa        60

<210> SEQ ID NO 22
<211> LENGTH: 60
<212> TYPE: DNA
<213> ORGANISM: Artificial Sequence
<220> FEATURE:
<223> OTHER INFORMATION: Homo sapiens N5 Neo-Pep-(17-36) polynucleotide

<400> SEQUENCE: 22
attgaatatc ttaagcagca agtttctcta cttaaggaga aagcaatttt gcaggcaact        60

<210> SEQ ID NO 23
<211> LENGTH: 60
<212> TYPE: DNA
<213> ORGANISM: Artificial Sequence
<220> FEATURE:
<223> OTHER INFORMATION: Homo sapiens N6 Neo-Pep-(19-38) polynucleotide

<400> SEQUENCE: 23
tatcttaagc agcaagtttc tctacttaag gagaaagcaa ttttgcaggc aactttgagg        60

<210> SEQ ID NO 24
<211> LENGTH: 60
<212> TYPE: DNA
<213> ORGANISM: Artificial Sequence
<220> FEATURE:
<223> OTHER INFORMATION: Homo sapiens N7 Neo-Pep-(21-40) polynucleotide

<400> SEQUENCE: 24
aagcagcaag tttctctact taaggagaaa gcaattttgc aggcaacttt gagggaagag        60

<210> SEQ ID NO 25
<211> LENGTH: 57
<212> TYPE: DNA
<213> ORGANISM: Artificial Sequence
<220> FEATURE:
<223> OTHER INFORMATION: Homo sapiens N8 Neo-Pep-(23-41) polynucleotide

<400> SEQUENCE: 25
caagtttctc tacttaagga gaaagcaatt ttgcaggcaa ctttgaggga agagaag        57

<210> SEQ ID NO 26
<211> LENGTH: 45
<212> TYPE: DNA
<213> ORGANISM: Artificial Sequence
<220> FEATURE:
<223> OTHER INFORMATION: Homo sapiens N9 Neo-Pep-(1-15) polynuceotide

<400> SEQUENCE: 26
gctgttctga agagactgga gcagaagggt gcagaggcag atcaa        45

<210> SEQ ID NO 27
<211> LENGTH: 45
<212> TYPE: DNA
<213> ORGANISM: Artificial Sequence
<220> FEATURE:
<223> OTHER INFORMATION: Homo sapiens N10 Neo-Pep-(12-26) polynucleotide

<400> SEQUENCE: 27
gaggcagatc aaatcattga atatcttaag cagcaagttt ctcta        45

<210> SEQ ID NO 28
<211> LENGTH: 45
<212> TYPE: DNA

<213> ORGANISM: Artificial Sequence
<220> FEATURE:
<223> OTHER INFORMATION: Homo sapiens N11 Neo-Pep-(13-27) polynucleotide

<400> SEQUENCE: 28

```
gcagatcaaa tcattgaata tcttaagcag caagtttctc tactt              45
```

<210> SEQ ID NO 29
<211> LENGTH: 45
<212> TYPE: DNA
<213> ORGANISM: Artificial Sequence
<220> FEATURE:
<223> OTHER INFORMATION: Homo sapiens N12 Neo-Pep-(17-31) polynucleotide

<400> SEQUENCE: 29

```
attgaatatc ttaagcagca agtttctcta cttaaggaga aagca              45
```

<210> SEQ ID NO 30
<211> LENGTH: 45
<212> TYPE: DNA
<213> ORGANISM: Artificial Sequence
<220> FEATURE:
<223> OTHER INFORMATION: Homo sapiens N13 Neo-Pep-(21-35) polynucleotide

<400> SEQUENCE: 30

```
aagcagcaag tttctctact taaggagaaa gcaattttgc aggca              45
```

<210> SEQ ID NO 31
<211> LENGTH: 45
<212> TYPE: DNA
<213> ORGANISM: Artificial Sequence
<220> FEATURE:
<223> OTHER INFORMATION: Homo sapiens N14 Neo-Pep-(27-41) polynucleotide

<400> SEQUENCE: 31

```
cttaaggaga aagcaattt gcaggcaact ttgagggaag agaag               45
```

<210> SEQ ID NO 32
<211> LENGTH: 936
<212> TYPE: DNA
<213> ORGANISM: Artificial Sequence
<220> FEATURE:
<223> OTHER INFORMATION: Homo sapiens AIMP1 polynucleotide

<400> SEQUENCE: 32

```
atggcaaata atgatgctgt tctgaagaga ctggagcaga agggtgcaga ggcagatcaa       60
atcattgaat atcttaagca gcaagtttct ctacttaagg agaaagcaat tttgcaggca      120
actttgaggg aagagaagaa acttcgagtt gaaaatgcta aactgaagaa agaaattgaa      180
gaactgaaac aagagctaat tcaggcagaa attcaaaatg gagtgaagca aataccattt      240
ccatctggta ctccactgca cgctaattct atggtttctg aaaatgtgat acagtctaca      300
gcagtaacaa ccgtatcttc tggtaccaaa gaacagataa aggaggaac aggagacgaa      360 aagaaagcga agagaaaat tgaaaagaaa ggagagaaga ggagaaaaa acagcaatca      420 atagctggaa gtgccgactc taagccaata gatgtttccc gtctggatct tcgaattggt      480
tgcatcataa ctgctagaaa acaccctgat gcagattctt gtatgtgga agaagtagat      540 gtcggagaaa tagccccaag gacagttgtc agtggcctgg tgaatcatgt tcctcttgaa      600
cagatgcaaa tcggatggt gatttttactt tgtaacctga acctgcaaa gatgagggga      660 gtattatctc aagcaatggt catgtgtgct agttcaccag agaaaattga atcttggct       720 cctccaaatg ggtctgttcc tggagacaga attacttttg atgctttccc aggagagcct      780
```

```
gacaaggagc tgaatcctaa gaagaagatt tgggagcaga tccagcctga tcttcacact    840
aatgatgagt gtgtggctac atacaaagga gttcccttg  aggtgaaagg gaagggagta    900
tgtagggctc aaaccatgag caacagtgga atcaaa                              936
```

```
<210> SEQ ID NO 33
<211> LENGTH: 312
<212> TYPE: PRT
<213> ORGANISM: Artificial Sequence
<220> FEATURE:
<223> OTHER INFORMATION: homo sapiens AIMP1 protein

<400> SEQUENCE: 33
```

Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
            20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Ala Phe
65                  70                  75                  80

Pro Ser Gly Thr Pro Leu His Ala Asn Ser Met Val Ser Glu Asn Val
                85                  90                  95

Ile Gln Ser Thr Ala Val Thr Thr Val Ser Ser Gly Thr Lys Glu Gln
            100                 105                 110

Ile Lys Gly Gly Thr Gly Asp Glu Lys Lys Ala Lys Glu Lys Ile Glu
        115                 120                 125

Lys Lys Gly Glu Lys Lys Glu Lys Lys Gln Gln Ser Ile Ala Gly Ser
    130                 135                 140

Ala Asp Ser Lys Pro Ile Asp Val Ser Arg Leu Asp Leu Arg Ile Gly
145                 150                 155                 160

Cys Ile Ile Thr Ala Arg Lys His Pro Asp Ala Asp Ser Leu Tyr Val
                165                 170                 175

Glu Glu Val Asp Val Gly Glu Ile Ala Pro Arg Thr Val Val Ser Gly
            180                 185                 190

Leu Val Asn His Val Pro Leu Glu Gln Met Gln Asn Arg Met Val Ile
        195                 200                 205

Leu Leu Cys Asn Leu Lys Pro Ala Lys Met Arg Gly Val Leu Ser Gln
    210                 215                 220

Ala Met Val Met Cys Ala Ser Ser Pro Glu Lys Ile Glu Ile Leu Ala
225                 230                 235                 240

Pro Pro Asn Gly Ser Val Pro Gly Asp Arg Ile Thr Phe Asp Ala Phe
                245                 250                 255

Pro Gly Glu Pro Asp Lys Glu Leu Asn Pro Lys Lys Lys Ile Trp Glu
            260                 265                 270

Gln Ile Gln Pro Asp Leu His Thr Asn Asp Glu Cys Val Ala Thr Tyr
        275                 280                 285

Lys Gly Val Pro Phe Glu Val Lys Gly Lys Gly Val Cys Arg Ala Gln
    290                 295                 300

Thr Met Ser Asn Ser Gly Ile Lys
305                 310

```
<210> SEQ ID NO 34
```

<211> LENGTH: 312
<212> TYPE: PRT
<213> ORGANISM: Artificial Sequence
<220> FEATURE:
<223> OTHER INFORMATION: homo sapiens AIMP1 protein

<400> SEQUENCE: 34

```
Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
            20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Ala Phe
65                  70                  75                  80

Pro Ser Gly Thr Pro Leu His Ala Asn Ser Met Val Ser Glu Asn Val
                85                  90                  95

Ile Gln Ser Thr Ala Val Thr Ala Val Ser Ser Gly Thr Lys Glu Gln
            100                 105                 110

Ile Lys Gly Gly Thr Gly Asp Glu Lys Lys Ala Lys Glu Lys Ile Glu
        115                 120                 125

Lys Lys Gly Glu Lys Lys Glu Lys Lys Gln Gln Ser Ile Ala Gly Ser
    130                 135                 140

Ala Asp Ser Lys Pro Ile Asp Val Ser Arg Leu Asp Leu Arg Ile Gly
145                 150                 155                 160

Cys Ile Ile Thr Ala Arg Lys His Pro Asp Ala Asp Ser Leu Tyr Val
                165                 170                 175

Glu Glu Val Asp Val Gly Glu Ile Ala Pro Arg Thr Val Val Ser Gly
            180                 185                 190

Leu Val Asn His Val Pro Leu Glu Gln Met Gln Asn Arg Met Val Ile
        195                 200                 205

Leu Leu Cys Asn Leu Lys Pro Ala Lys Met Arg Gly Val Leu Ser Gln
    210                 215                 220

Ala Met Val Met Cys Ala Ser Ser Pro Glu Lys Ile Glu Ile Leu Ala
225                 230                 235                 240

Pro Pro Asn Gly Ser Val Pro Gly Asp Arg Ile Thr Phe Asp Ala Phe
                245                 250                 255

Pro Gly Glu Pro Asp Lys Glu Leu Asn Pro Lys Lys Lys Ile Trp Glu
            260                 265                 270

Gln Ile Gln Pro Asp Leu His Thr Asn Asp Glu Cys Val Ala Thr Tyr
        275                 280                 285

Lys Gly Val Pro Phe Glu Val Lys Gly Lys Gly Val Cys Arg Ala Gln
    290                 295                 300

Thr Met Ser Asn Ser Gly Ile Lys
305                 310
```

<210> SEQ ID NO 35
<211> LENGTH: 312
<212> TYPE: PRT
<213> ORGANISM: Artificial Sequence
<220> FEATURE:
<223> OTHER INFORMATION: homo sapiens AIMP1 protein

<400> SEQUENCE: 35

```
Met Ala Asn Asn Asp Ala Val Leu Lys Arg Leu Glu Gln Lys Gly Ala
```

```
            1               5                  10                 15
         Glu Ala Asp Gln Ile Ile Glu Tyr Leu Lys Gln Gln Val Ser Leu Leu
                         20                 25                 30

Lys Glu Lys Ala Ile Leu Gln Ala Thr Leu Arg Glu Glu Lys Lys Leu
                         35                 40                 45

Arg Val Glu Asn Ala Lys Leu Lys Lys Glu Ile Glu Glu Leu Lys Gln
                 50                 55                 60

Glu Leu Ile Gln Ala Glu Ile Gln Asn Gly Val Lys Gln Ile Ala Phe
         65                 70                 75                 80

Pro Ser Gly Thr Pro Leu His Ala Asn Ser Met Val Ser Glu Asn Val
                         85                 90                 95

Ile Gln Ser Thr Ala Val Thr Thr Val Ser Ser Gly Thr Lys Glu Gln
                         100                105                110

Ile Lys Gly Gly Ala Gly Asp Glu Lys Lys Ala Lys Glu Lys Ile Glu
                         115                120                125

Lys Lys Gly Glu Lys Lys Glu Lys Lys Gln Gln Ser Ile Ala Gly Ser
                         130                135                140

Ala Asp Ser Lys Pro Ile Asp Val Ser Arg Leu Asp Leu Arg Ile Gly
         145                150                155                160

Cys Ile Ile Thr Ala Arg Lys His Pro Asp Ala Asp Ser Leu Tyr Val
                         165                170                175

Glu Glu Val Asp Val Gly Glu Ile Ala Pro Arg Thr Val Val Ser Gly
                         180                185                190

Leu Val Asn His Val Pro Leu Glu Gln Met Gln Asn Arg Met Val Ile
                         195                200                205

Leu Leu Cys Asn Leu Lys Pro Ala Lys Met Arg Gly Val Leu Ser Gln
                 210                215                220

Ala Met Val Met Cys Ala Ser Ser Pro Glu Lys Ile Glu Ile Leu Ala
         225                230                235                240

Pro Pro Asn Gly Ser Val Pro Gly Asp Arg Ile Thr Phe Asp Ala Phe
                         245                250                255

Pro Gly Glu Pro Asp Lys Glu Leu Asn Pro Lys Lys Ile Trp Glu
                         260                265                270

Gln Ile Gln Pro Asp Leu His Thr Asn Asp Glu Cys Val Ala Thr Tyr
                         275                280                285

Lys Gly Val Pro Phe Glu Val Lys Gly Lys Gly Val Cys Arg Ala Gln
                         290                295                300

Thr Met Ser Asn Ser Gly Ile Lys
         305                310

<210> SEQ ID NO 36
<211> LENGTH: 21
<212> TYPE: DNA
<213> ORGANISM: Artificial Sequence
<220> FEATURE:
<223> OTHER INFORMATION: Forward primer for TCF7

<400> SEQUENCE: 36
atccttgatg ctgggattct g                                      21

<210> SEQ ID NO 37
<211> LENGTH: 21
<212> TYPE: DNA
<213> ORGANISM: Artificial Sequence
<220> FEATURE:
<223> OTHER INFORMATION: Reverse primer for TCF7
```

```
<400> SEQUENCE: 37
cttctcttgc cttgggttct g                                              21

<210> SEQ ID NO 38
<211> LENGTH: 18
<212> TYPE: DNA
<213> ORGANISM: Artificial Sequence
<220> FEATURE:
<223> OTHER INFORMATION: Forward primer for AXIN2

<400> SEQUENCE: 38
ctccttggag gcaagagc                                                  18

<210> SEQ ID NO 39
<211> LENGTH: 18
<212> TYPE: DNA
<213> ORGANISM: Artificial Sequence
<220> FEATURE:
<223> OTHER INFORMATION: Reverse primer for AXIN2

<400> SEQUENCE: 39
ggccacgcag caccgctg                                                  18

<210> SEQ ID NO 40
<211> LENGTH: 22
<212> TYPE: DNA
<213> ORGANISM: Artificial Sequence
<220> FEATURE:
<223> OTHER INFORMATION: Forward primer for CD44

<400> SEQUENCE: 40
ccacagcctc ctttcaataa cc                                             22

<210> SEQ ID NO 41
<211> LENGTH: 19
<212> TYPE: DNA
<213> ORGANISM: Artificial Sequence
<220> FEATURE:
<223> OTHER INFORMATION: Reverse primer for CD44

<400> SEQUENCE: 41
ggagtcttcg cttggggta                                                 19
```